US005824331A

United States Patent [19]
Usala

[11] Patent Number: 5,824,331
[45] Date of Patent: Oct. 20, 1998

[54] BIOARTIFICIAL DEVICES AND CELLULAR MATRICES THEREFOR

[75] Inventor: Anton-Lewis Usala, Winterville, N.C.

[73] Assignee: Encelle, Inc.

[21] Appl. No.: 568,503

[22] Filed: Dec. 7, 1995

Related U.S. Application Data

[63] Continuation-in-part of Ser. No. 300,429, Sep. 2, 1994, abandoned, which is a continuation-in-part of Ser. No. 841,973, Feb. 24, 1992, abandoned.

[51] Int. Cl.⁶ .............................. A61F 2/02; A61K 47/30; C12N 11/04
[52] U.S. Cl. ...................... 424/424; 514/772.3; 623/11; 435/182
[58] Field of Search ................................. 424/423, 424; 435/1.1, 182; 623/11; 514/772.3

[56] References Cited

U.S. PATENT DOCUMENTS

| | | | |
|---|---|---|---|
| 4,696,286 | 9/1987 | Cochrum | 435/1.1 |
| 4,797,213 | 1/1989 | Parisius et al. | 210/651 |
| 4,868,121 | 9/1989 | Scharp et al. | 435/268 |
| 5,079,160 | 1/1992 | Lacy et al. | 435/240.2 |
| 5,322,790 | 6/1994 | Scharp et al. | 435/268 |

FOREIGN PATENT DOCUMENTS

| | | | |
|---|---|---|---|
| WO 92/19195 | 11/1992 | WIPO | A61F 13/00 |
| WO 93/16685 | 9/1993 | WIPO | A61K 9/14 |
| WO 95/19430 | 7/1995 | WIPO | C12N 11/10 |

OTHER PUBLICATIONS

P. Metrakos et al., *Collagen Gel Matrix Promotes Islet Cell Proliferation, Trnasplantation Proceeds* 26(6):3349–3350 (1994).

*Primary Examiner*—Carlos Azpuru
*Attorney, Agent, or Firm*—Alston & Bird, LLP

[57] ABSTRACT

A device for the effective release of cellular moieties, including hormones, wherein a matrix containing a hormone producing cellular moiety is encapsulated with a nonimmunogenic polymeric material of poly-para-xylylene or other aromatic based polymeric moiety having a membrane portion with a porosity blocking passage therethrough of immunogenic agents and permitting passage therethrough of effective nutrients for said cellular moiety and the hormone produced thereby, an improved matrix for the storage, manufacture, functional testing, and viral infection testing of cellular moieties wherein a collagen based hydrogel is processed to present a liquid phase at host temperature and functions as a substrate for cellular attachment with additives effective for limiting thermal and pressure trauma, and an improved method for the harvesting tissue from organs.

51 Claims, 20 Drawing Sheets

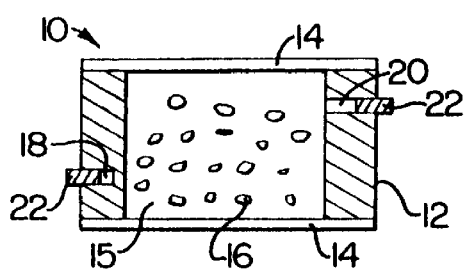
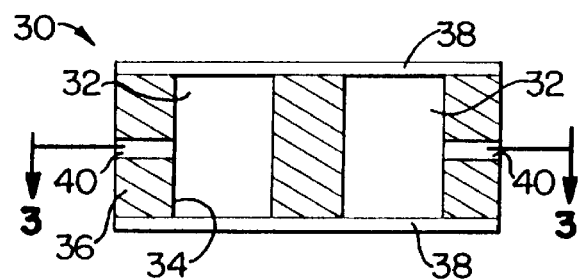
FIG. 1.  FIG. 2.
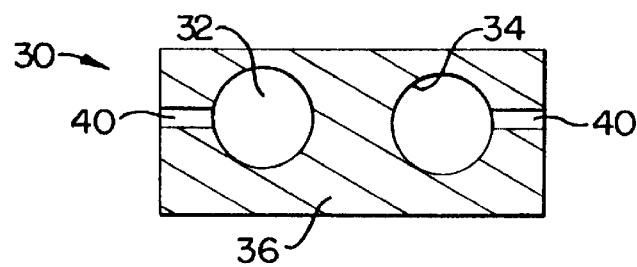
FIG. 3.
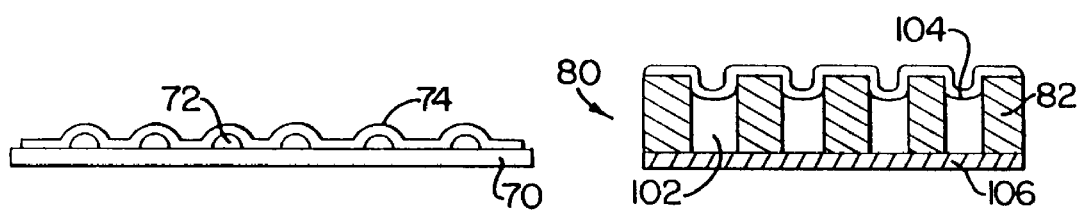
FIG. 4.  FIG. 5.

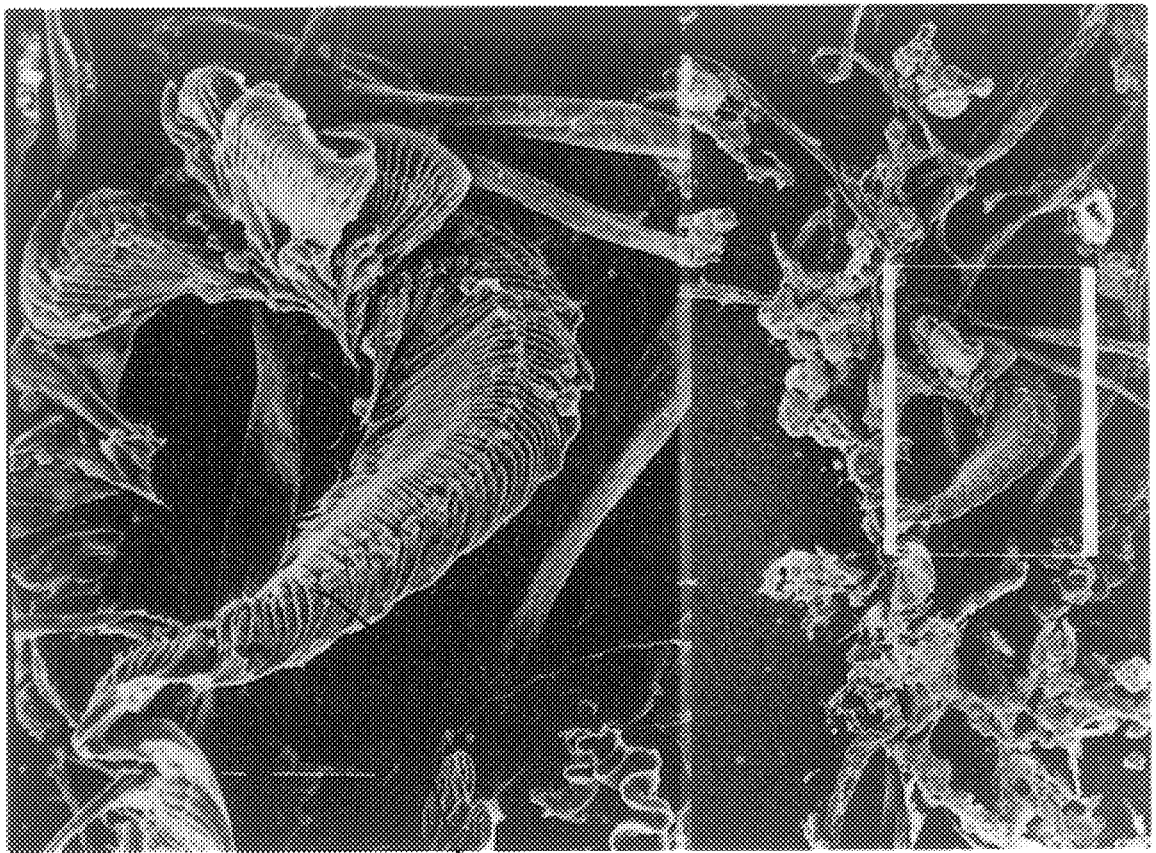
FIG. II.

BIOARTIFICIAL DEVICES AND CELLULAR MATRICES THEREFOR

RELATED APPLICATIONS

This application is a continuation-in-part application of U. S. patent application Ser. No. 08/300,429 filed on Sep. 2, 1994, now abandoned, which is a continuation-in-part application of U. S. Ser. No. 07/841,973 filed on Feb. 24, 1992, now abandoned.

BACKGROUND OF THE INVENTION

The present invention relates to the encapsulation of cellular moities, including hormone producing tissue, and, in particular, to the membrane encapsulation of insulin producing pancreatic islets for xenographic transplantation into diabetic subjects. Additionally, the present invention relates to an improved matrix for tissue and, in particular, hormone producing tissue which permits long term storage of the tissue, periodic assessment of tissue functionality, non-destructive testing of tissue containing devices prior to transplantation, and which promotes tissue growth therein.

Diabetes Mellitus is an affliction affecting approximately 20 million persons in the United States of America alone. This affliction is characterized by either a near total lack of insulin (Type I diabetes) or a resistance to normal levels of circulating insulin (Type II diabetes). Both conditions can currently be controlled to some extent by daily subcutaneous injections of exogenous insulin. Because the insulin injections are periodically spaced in predetermined doses, the regimen functions as an open loop system, not releasing insulin in accordance with metabolic demand and thereby not regulating blood glucose levels within ranges achieved by normal non-diabetic subjects. Accordingly, it is well recognized that this type of therapy has failed to achieve the necessary metabolic control of blood sugar to prevent the vascular complications associated with the disease. These complications include blindness, kidney failure, heart disease, stroke, and loss of peripheral sensory nerve function. In addition, it is medical consensus that the loss or normal insulin pulsatility, whereby insulin is released approximately every ten minutes in discrete boluses, is required to maintain mormal insulin sensitivity, both in Type I and Type II diabetes. Loss of this normal pulsatility and worsening of insulin resistance is thought to be of primary importance in the development of large vessel disease associated with diabetes. Diabetes currently is the third largest disease cause of death in the United States, costing approximately $2–3 billion a year for treatment.

Insulin dispensing pumps, programmed or manually operated, for delivering insulin to the diabetic subject have been used to provide more numerous, smaller doses of insulin in an attempt to regulate blood glucose within narrower ranges. Such pumps, nonetheless still function as an open loop system, only attempting to anticipate, but not respond to metabolic demand. Because the insulin from such pumps normally must be absorbed through subcutaneous tissue, there is no discrete bolus of insulin dispensed. The therapeutic efficacy of current pumps over conventional insulin injection is not clearly established or clinically accepted. There have been attempts to regulate pumps with blood glucose sensors to provide closed loop control, but to date an implantable sensor with long term biocompatibility and functionality has not been achieved.

Medical researchers for many years have recognized the desirability of closed loop implantable devices incorporating live insulin producing tissue, islets or isolated beta cells, which through a selective, permeable membrane, release insulin in accordance with metabolic demand. These devices, termed "bioartificial pancreases" have been defined in terms of functional and performance constraints. First, the tissue must respond and release insulin in required amounts within an appropriate time to increases and decreases in blood glucose concentration. Second, the device must support and not suppress insulin production. Third, the device must provide protection against immune rejection. Fourth, the islets must survive functionally or the device easily replaced. Fifth, the membrane must be appropriately selective and biocompatible with the patient and its functional properties not altered by contact with host tissue.

Various capsule approaches have been taken with regard to physical devices containing islets, using planar or tubular membranes. Examples of membranes that have been proposed in the art include Amicon hollow fibers, alginate polylysine capsules, polyacrylonitrile sheets and hollow fibers, agarose gel capsules, Millipore membranes, modified collodion, cellulose acetate, polyvinyl difluoride, polypropylene, polyethylene, Nuclepore membranes from Nuclepore Corporation, Poretic membranes from Poretic Corporation and others. Generally, these have failed due to lack of biocompatibility leading to fouling of the membrane as well as being too thick when applied to islet tissue to adequately allow a physiologic glucose signal in and release of insulin out. In attempts to overcome rejection, highly purified beta cells have been implanted into human subjects taking large doses of effective immunosuppressants such as cyclosporin. As far as known, there have not been any long term successful implantations using this approach.

Recently, islets have been macroencapsulated in a hydrogel such as sodium alginate and injected into hollow fibers formed by a dry-wet spinning technique using an acrylic copolymer. While demonstrating an ability to control glucose levels in mice, the long term biocompatibility of the fibers has not be established.

BRIEF SUMMARY OF THE INVENTION

The present provides an implantable device satisfying the above criteria while overcoming the aforementioned problems to provide closed loop insulin delivery in accordance with demand and overcoming the above problems of rejection by selectively protecting the pancreatic islets from the host's immune defenses by a recognized biocompatible material. More particularly, the islets, human or preferably animal which are more readily available, in either cellular form or within enclosure devices, are encased with a polymeric material comprising poly-para-xylylene having a membrane portion with a porosity permitting passage of nutrients, glucose signals, electrolytes, water, and the egress of insulin released by the islets, all of which have a molecular weight of less than about 6,000. The porosity of the membrane, however, is less that immunoglobulins and antibodies having molecular weights of 40,000–500,000. Poly-para-xylylene in particular is recognized as a biocompatible surface substrate for implantation and does not to interact with plasma factors such as fibrin or cells such as platelets. Accordingly, the capsule pores will not become clogged, and insulin release as a function of the host's own glucose concentration will be effected. The device may take various designs based on fresh or frozen islets and configured in various cell arrays, while providing the selective membrane porosity of the poly-para-xylylene and biocompatibility for the interior and exterior surfaces thereof.

The present invention also provides a method for the conformal coating of the device with a selectively permeable membrane using a hydrogel matrix. The method permits the coating of islet containing hydrogel matrices, under high vacuum conditions, without cellular damage or erosion of the hydrogel. Because of the conformal nature and thickness of the coating, the present invention uniquely allows very rapid insulin response to a glucose signal, thus allowing physiologic insulin pulsatility to occur.

The present invention further provides an improved cellular matrix which allows long term storage of cellular moieties including islets, periodic testing of their functionality, an improved substrate for application of the membrane, non-destructive testing of the cellular moieties and associated devices, and long term storage of such devices. Post manufacture testing of device functionality may be conducted prior to transplant. Moreover, the matrix provides an environment promoting islet replication and replication of other cellular moieties. Heretofore, those skilled in the art of islet transplantation needed to proceed directly from islet isolation and purification to device manufacture, all within a matter of days. Post device manufacture, the devices were implanted without the ability to nondestructively test device functionality. The present invention provides a matrix resembling the native pancreatic system comprising a collagenous and/or gelatinous base to which the islets attach and thrive. More particularly, the matrix utilizes a boiled collagen which together with media and additives provides polymeric strands to which the islets, singularly and in clusters, attach. Matrix formulations, as described in greater detail below, have sustained the functionality of the islets in storage for greater than six months without contamination, permitted storage of completed devices for months with the ability to functionally test prior to implant, extended longevity in-vivo without decrease in performance and with indications of improved insulin production with time. Further, the matrix supplementally applied over the transplanted device has promoted vascularization in the immediate vicinity of the membrane.

The present invention provides a cellular matrix utilizing a substrate for cellular attachment of islets, hepatocytes or the like, based on thermally dependent hydrogen bond formation and dipole moment interactions. Preferable substrates include in part collagen based gelatin which provides a natural milieu for cellular growth, and contains polar and non-polar amino acids that readily form a gel when boiled or otherwise denatured based on amine, carboxyl group, hydroxyl group, and sulfhydryl group hydrogen bond formation and dipole moment interactions. The resistance of the matrix to force can be increased by the addition of chelators that remove divalent cation interference from the hydrogen bond and dipole moment interactions. Exposed active groups are used to immobilize water at lower temperatures via this hydrogen bond formation, thus minimizing thermal trauma at lower temperatures.

The present invention further provides a cellular matrix that yields protection from nitric oxide and its metabolites, which are known to cause cellular death from nuclear damage (apoptosis) and other related injuries. The cellular matrix utilizes amino acids and related compounds which serve to inhibit L-arginine from forming nitric oxide through nitric oxide synthase, either consituitive or inducible. Cysteine, in particular, and other related compounds with sulfhydryl groups that are found in collagenous material also serve to scavenge nitric oxide and thus limit its deleterious (or beneficial) properties.

The present invention still further provides a cellular matrix that includes a metabolically stable cryopreservant that provides an inert cushion to thermally dependent cellular expansion and contraction. A preferred cryopreservant is sulfated dextran wherein the sulfhydryl groups provide sites for disulfide linkages and increased matrix resistance to force, as well as inhibiting nitric oxide accumulation. Such sulfated groups also provide sites for binding of growth factors such as IGF-I and IGF-II, known by those skilled in the art to be required for continued islet growth and maintenance.

The present invention yet further provides an improved method for the digestion using enzymic solution for releasing a desirable cellular moiety wherein an effective amount of a nitric oxide inhibitor is added to the solution in a manner that increases endothelial rigidity and results in improved enzymic cleavage.

Those skilled in the art of biological transplantation will appreciate that devices and matrices as briefly described will find application in the various transplantation therapies, including without limitation cells secreting human nerve growth factors for preventing the loss of degenerating chlolinergic neurons, satellite cells for myocardial regeneration, striatal brain tissue for Huntington's disease, liver cells, bone marrow cells, dopamine-rich brain tissue and cells for Parkinson's disease, cholinergic-rich nervous system for Alzheimer's disease, adrenal chromaffin cells for delivering analgesics to the central nervous system, cultured epithelium for skin grafts, and cells releasing ciliary neurotropic factor for amyotrophic lateral sclerosis.

BRIEF DESCRIPTION OF THE DRAWINGS

The above and other features and advantages of the present invention will become apparent upon reading the following written description of the preferred embodiments, taken in conjunction the accompanying drawings in which:

FIG. 1 is a side cross sectional view of bioartificial endocrine device in accordance with an embodiment of the present invention;

FIG. 2 is a side cross sectional view of another embodiment of the present invention;

FIG. 3 is a cross sectional view taken along line 3—3 in FIG. 2;

FIG. 4 is a side cross sectional view of another embodiment of the present invention;

FIG. 5 is a cross sectional view of a further embodiment of the invention;

FIG. 11 is an enlarged view of a portion of FIG. 6 showing cluster of islets attached to denatured collagen strands and an inset enlargement showing an intact strand of collagen;

DESCRIPTION OF THE PREFERRED EMBODIMENTS

Figure 6:
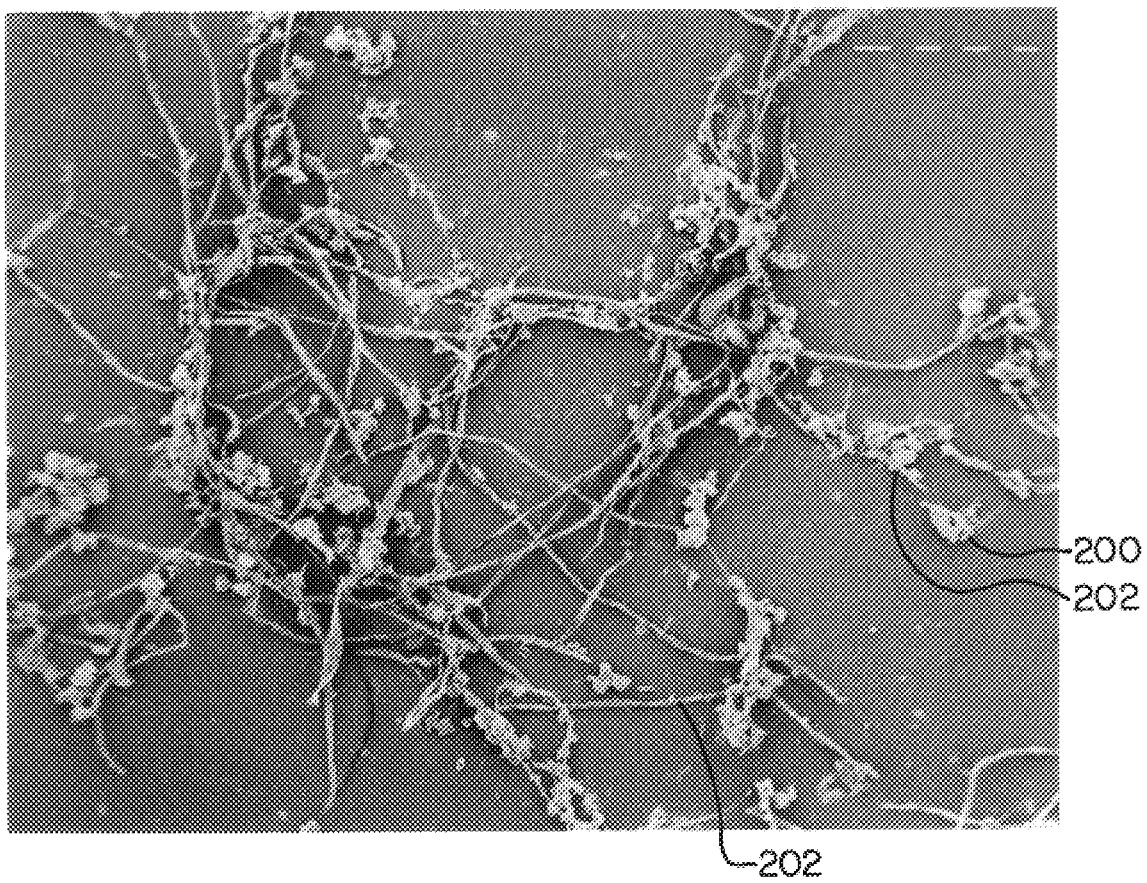
FIG. 6 is a scanning electromicrograph showing attachment of clusters of islets to collagenous fibers of a further matrix.

The present invention has particular utility in the providing of biological substances normally produced by cellular moieties that are normally associated with the endocrine glands, such as the pancreas, thyroid, parathyroid, thymus, pituitary, adrenal cortex, and adrenal medulla. Cellular moieties of the pancreas and pituitary are preferred. As used herein, cellular moieties include both naturally occuring and genetically altered cells that secrete both naturally occuring substances and analogs thereof, synthetic or otherwise. Cells useful in the method of the present invention include, but are not limited to, somatotrophs, lactotrophs, thyrotrophs, gonadotrophs, and corticolipotrophs.

The biological substances provided by the method of the present invention are typically referred to as hormones. As used herein, a "hormone" is defined as a biological substance secreted by a specific tissue, and includes those substances having an activity at the site of secretion, sometimes called autocoids, and precursors thereof. Exemplary hormones include peptides, proteins, glycoproteins, fats, lipids, polysccharides, and carbohydrates. Peptides are preferred, with the term "peptide" as used herein referring to a peptide as a discrete molecule or residing in a protein.

Hormones secreted by the pituitary gland, or adenohypophysis, include the growth hormones (GH), prolactin, gonadotropins, thyrotropin, corticotropin, melanocyte-stimulating hormones, somatomedins, and lipotropins.

Gonadotropins are glycoproteins generally secreted by the pituitary gland, and include follicle stimulating hormone (FSH), luteinizing hormone (LH or ICSH), chlorionic gonadotropin (CG), thyrotropin (TSH), individual peptide chains thereof, and carbohydrates associated therewith. These hormones, along with hormones of estrogen, progestin, and androgen families, may be useful in the treatment of infertility. Gonadotropin releasing hormones, such as follicle stimulating hormone releasing hormone (FSHRH) or lutenizing hormone releasing hormone (LHRH), are also provided by the present invention.

Melanocyte-stimulating hormones include corticotropin (ACTH), alpha-melanocyte-stimulating hormone (alpha-MSH), beta-melanocyte-stimulating hormone (beta-MSH), beta-lipotropin (beta-LPH), gamma-lipotropin (gamma-LPH), and their common precursor, pro-opiomelanocortin.

Somatomedins are a family of peptide hormones that range from about 7,000 to 8,000 daltons in molecular weight, and are similar to growth factors, such as nerve growth factor (NGF), epidermal growth factor (EGF) and fibroblast growth factor (FGF). One exemplary somatomedin is the insulin-like growth factor (IGF). Growth factors themselves, such as tissue growth factors, are further encompassed by the scope of this invention to promote skin/bone growth and promote wound healing. Growth factors are provided by the present invention in both small and large forms.

Exemplary hormones secreted by the parathyroid are the parathyroid hormone and its precursor, proparathyroid hormone. The hormone calcitonin and prolactin are secreted by the thyroid, parathyroid and thymus. Prolactin a, like the growth factors, occur naturally in both small and large forms, both of which are provided by the celluair moities of the present invention. Hormones normally secreted by the adrenal cortex may be further provided by the practice of this invention, including adrenocortical steroids, such as adrenocorticotropic hormone, and their synthetic analogs.

The present invention may also be used to provide cellular moities that are normally found within the brain and which secrete neurologically active substances. Therefore, neuropeptides may be provided in the practice of the invention, including the neuropeptides families of the endorphins, the glucagon-secretins, and the substance P neuropeptides. Endorphins include the prooopimelanocortins, the proenkephalins, the prodynorphins and hormones derived therefrom. The glucagon-secretins include glucagon, vasoactive intestinal polypeptide, both found in pancreatic islets, secretin and growth hormone releasing factor (GHRF) . The substance-P neuropeptides include vasotocin, vasopressin and oxytocin. It is specifically intended that substances secreted by single large clusters of neurons, such as oxytocin, vasopressin, LHRH, GHRH, and proopiomelanocortin, are embraced by the scope of the invention, as well as substances secreted by cells normally distributed throughout the brain, such as somatostatin, cholecystokinin and enkephalin.

The present invention may also be used to provide mast cells as a particular cellular moiety. It is a further aspect of the invention, therefore, that substances secreted by these cells, including those in the histamine family and synthetic analogs thereof, such as pentagastrin, are provided in the method of the invention.

Other biological substances that may be provided by the cellular moities of the present invention include, but are not limited to, the following: polypeptide autocoids (i.g. aldosterone), the plasma kinins (e.g. bradykinin and kallidin, the autogiotensins eosinophil chemotactic factor (ECFA), neutrophil chemotactic factor (NCFA), peptide-based immunosuppressand useful in the treatment of organ rejection in transplants, human granulocyte colony stimulating factor useful in facilitating bone marrow transplantation, T-cell receptor peptide useful in treating autoimmune and connective tissue disorders, disaccharide peptide, immunostimulants, platelet derived growth factor (PDGF), amylin, glucagon, pramintide, and thrompoetin.

While the present invention is concerned primarily with the treatment of human subjects, it may be employed for the treatment of other mammalian subjects, such as cows, pigs, goats, cats, and dogs, for veterinary purposes. For example, one embodiment of the invention is an implant for secreting hormones and the like in animals for veterinary and/or agricultural purposes such as somatotropin for increasing milk production of cows, goats, or any other milk-producing animal. Growth hormones may also be administered to an animal subject for the purposes of increasing milk production.

The preferred embodiments described in detail below have primary reference to bioartificial endocrine devices for implantation to overcome endocrine deficiencies in a recipient patient, particularly a bioartificial pancreas wherein insulin producing cellular moities release insulin in response to changes in serum glucose. However, those skilled in the art will appreciate that research has been conducted on a broad basis for implanting living cells into a recipient to treat various cell and molecular deficient diseases. These implanted cells are targeted for generating biological products that the recipient cannot produce for itself as a result of disease, injury or other disabling reasons.

Referring to the drawings for purposes of describing the preferred embodiments only, FIG. 1 shows a bioartificial endocrine device 10 for the effective release of hormones. The device comprises a circular cylinder 12 having a pair of selective permeable membranes 14 attached by a biocompatible adhesive to the top and bottom end faces thereof. A suitable adhesive for attachment of the membrane to the sleeves and the sleeves to each other are silicone adhesive, Silastic Type A manufacture by Dow-Corning, cyanoacrylates, Prism 454 manufactured by Locktite Corporation, epoxies or other adhesives, preferably biocompatible, providing sufficient adhesion to sealingly maintain the integrity of the cavity. The interior volume or chamber 15 is defined by the inner wall of the cylinder 12 and the membranes 14. The chamber 15 contains hormone producing tissue, preferably porcine pancreatic islets, or other hormone producing cellular moieties 16 in a liquid or gel matrix. The term matrix is used herein in accordance with its accepted meaning in the art as materials in which tissues are carried. In addition to those described herein, the matrix may be alginate based (Schrezenmeir, J. et al, Transplantation 57: 1308–14, 1994), agar or agarose based (Iwata, H. et al, Diabetes 38: 224–225, 1989).

Prior to filling, the assembled device is heat or gamma radiation sterilized. The side wall of the cylinder is provided with a lower radial port 18 for introducing the cellular matrix into the chamber 15 and an upper radial port 20 for venting the chamber 15 during filling. The ports 18, 20 are sealed by sterile biocompatible members 22.

The cylinder 12 may be formed of any suitable material, such as metal or plastic. The membranes 14 are polymeric films of poly-para-xylylene (poly-para-xylylene N), or analogs thereof such as poly-monochloro-xylylene (poly-para-xylylene C), and poly-dichloro-xylylene (poly-para-xylylene D), commonly referred to as paralene, and mixtures thereof. The membranes 14 have a porosity which permits passage therethrough of effective nutrients for the cellular moiety and the hormone produced thereby. For a bioartificial pancreatic device, as described below, membranes comprising poly-para-xylylene N at a thickness of about 2,000 to 5,000 Angstroms, and preferably about 2,500 to 3,500 Angstroms, provide the desired porosity characteristics. The lower limit may be below the foregoing as long as the thickness does not result in insufficient membrane strength.

The membranes are formed by conventional vacuum deposition and have a porosity which can be accurately controlled such that a selective membrane may be established. As mentioned above, the paralene coating may be applied using conventional equipment available from Specialty Coatings System of Indianapolis, Ind. or Para Tech Coating, Inc. of Aliso Viejo, Calif., who also supply the paralene dimer. The equipment is available in various configurations which can apply a coating to exacting specifications. One particular machine configuration is set forth in the U.S. Pat. No. 4,683,143 issued to Riley. Basically, all such systems use a vaporizer connected to a pyrolizer that is in turn connected to a vacuum chamber evacuated by a cold trap protected vacuum pump. Under vacuum and heat, the paralene dimer is vaporized in the vaporizer and passes to the pyrolizer wherein the dimer is thermally cleaved to a monomer which is conformally deposited on the devices in the chamber, at ambient temperature, as a long chain polymer. As is well known, the thickness of the coating on coated parts may be determined by locating a planar witness plate in the coater during the coating process. Inasmuch as the entire chamber, fixture and parts receive a substantially uniform coating, the witness plate may be removed and tested by conventional thickness measuring apparatus to thereby determine the thickness on the coated part. This is a convenient procedure for preformed films, as described in some of the embodiments below. However, when the coating is applied over a hydrogel matrix as described in other embodiments below, it is noticed that cooling of the matrix occurs due to outgassing of liquids, resulting is in variations in the thickness between the witness plate and the applied membrane as visually observable on the basis of color variations therebetween, the paralene having a distinctive coloration spectrum versus thickness. At the present time, Applicant is not aware of available thickness measuring equipment for providing direct measurement of membrane thickness under these conditions. Nonetheless, the specific attributes of the membrane devices in accordance with the present invention may be determined by functional in vitro testing as supplemented by the basic parameter requirements as noted below.

In the present invention, the maximum pore size is selected to prevent passage of immunoglobulins and antibodies having molecular weights of 40,000 to about 500,000. The minimum pore size is selected to permit the passage of nutrient molecules, such as glucose, electrolytes and water, and the hormone, insulin having a molecular weight of around 5,600. For other cellular moieties, the aforementioned maximum porosity is likewise applicable, however the minimum porosity, as those skilled in the art will understand, would be dependent on the biological product released. For example, a device for treatment of Parkinson's disease containing substantia migra cells isolated from brain tissue would require molecular weight cut off of at least 1000 to allow passage of dopamine and related compounds, whereas treatment of hypothyroidism treated by isolated thyroid tissue would require a molecular weight cut off of only 500 to allow transfer of thyroid hormone.

The invention may utilize any polymer that utilizes primarily aromatic rings instead of aliphatic chains inasmuch as the aromatic rings provide fewer chemical binding sites in vivo than do the straight chain carbon polymers with active chemical sites. Because aromatic polymers such as paralene do not have readily available binding sites, the subject's immune system does not recognize it as foreign and is unable to bind to its surface, thus leaving the molecular pores unclogged. Other such polymers include poly phenyl oxide, poly phenyl sulfide, poly phenyl amine and other polymers having repeating aromatic moieties.

EXAMPLE 1

A membrane of poly-para-xylylene N having a thickness of 3,271 Angstroms was mounted on a cylindrical sleeve and partially immersed in distilled water. A liquid containing components of varying molecular weights was placed on the upper surface of the membrane. Thereafter samples of the water were applied to an SDS-PAGE gel and subjected to electrophoresis to separate the samples according to molecular weights. Low molecular weights corresponding to glucose, insulin and cell nutrients were identified. Higher molecular weight components, i.e. greater than 26,000 were excluded.

More particularly, for an implantable bioartificial pancreatic device, the cellular moiety contains a plurality of insulin producing islets. The islets are derived from donor pancreatic organs, both human and animal, in conventional manner utilizing collagenous digestion and Ficoll or Dextran, gradient separation. The islets are admixed with conventional RPMI culture media to form the matrix at a concentration of around 10 to 50 islets per microliter.

The cylinder may vary in size and shape for purpose of handling, coating and implantation considerations as well as the therapeutic insulin production required by the recipient.

For purposes of implant biocompatibility, the cylinder may be formed of a suitable material such a medical grade stainless steel or preferably by conformal coating the poly-para-xylene, the thickness of which is not particularly critical, however a coating thickness of about 0.5 microns is preferred. This coating may be precisely applied in controlled thicknesses according to conventional techniques. The coating and membrane materials are recognized as non-immunogenic substrates for human implantation. The material does not interact with plasma factors such as fibrin or cells such as fibroblasts, macrophages or platelets. Accordingly, the device and membrane pores will not become clogged or impair insulin release as a function of the host tissue growth.

EXAMPLE 2

A membrane of poly-para-xylylene N at a thickness of around 3,100 Angstroms was mounted on a cylindrical sleeve and partially immersed in a media, distilled water. Seventy-five (75) adult porcine islets were placed in RPMI culture media on the top surface of the membrane. The media was periodically sampled and changed after each sampling. Two aliquots were extracted from the media on the fourth and sixth days. The aliquots were tested in duplicate in an $^{125}$I Insulin RIA (Ventrex). Insulin levels on the sample from the fourth day was 70+149 uU/ml and on the sample from the sixth day was 235+150 uU/ml, demonstrating that insulin secreted from the islets traversed the membrane. No fibrin or other cell attachment occurred.

EXAMPLE 3

An implant device was prepared using two PVC sleeves, ½" O.D., ⅜" I.D., 3/16" thickness. The sleeves were coated with poly-para-xylylene N to a thickness of about 0.5 microns. Circular poly-para-xylylene membranes having a thickness of 2,959 Angstroms were adhered to the top surfaces of the sleeves with silicone adhesive. The sleeves were then radiation sterilized.

One membrane sleeve was filled with 20 deciliter of cellular matrix. The matrix included porcine beta cell islets numbering about 5,000. The islets were prepared in accordance with the collagenase digestion method. Thereafter the sleeves were joined with a silicone adhesive. The device was implanted into the peritoneal cavity in a non-obese diabetic mouse.

For three weeks prior to implant, the fasting blood glucose (FBG) of the mouse was 760 mg/dl as determined by glucose oxidase analysis. On the day following implantation, the fasting blood glucose level was 380 mg/ml. When the device was removed following implant, no fibroid or lymphoblastic attachment to the device or the membrane was observed.

EXAMPLE 4

An implant device was constructed in accordance with the embodiment of FIG. 1. The collar had an outside diameter of ½ inch and an inner diameter of ¼ inch. A membrane of around 3,000 A poly-para-xylylene N was adhered to the faces of the collar with a silicone adhesive. Through radial fill holes the interior volume of the device was filled with approximately 5,000 adult porcine islets. The fill hole was sealed with a silicone plug. Four such devices were implanted into the peritoneal cavity of a pancreatized female mongrel dog weighing about 12 kg. The first day following implant, the plasma insulin levels were measured at 21.2 and 22.2 uU/ml. On the second day following implant, the plasma insulin levels were measure at 21.5 and 20.5 uU/ml.

Referring to FIGS. 2 and 3, a device 30 is provided with a plurality of cylindrical chambers 32 as defined by an array of through holes in a generally rectangular poly-para-xylene coated plate 36. The top and bottom of the holes 34 are sealed by poly-para-xylylene membranes 38 as described above. Cellular tissue in a liquid matrix is delivered to the chambers 32 through radial fill ports 40 which are thereafter sealed by plugs. The array of chambers 32 provides redundancy for the device in the event of membrane breakage or fouling, decrease in cellular output and the like.

Referring to FIG. 4, a device comprises a plate 70 having a plurality of cellular droplets 72 arrayed thereon and covered with a membrane 74 of poly-para-xylylene as described above. The device is formed by depositing the tissue media in liquid form or macroencapsulated in a protective covering, such as sodium alginate, on an poly-para-xylylene coated plate. After deposition, the droplets and plate are coated to the desired thickness with poly-para-xylylene. Alternatively, the droplets and plate are frozen, coated, and, when ready for implant, the device is thawed to reconstitute the cells, The cells may be frozen and thawed according to the protocol set forth in R. V. Rajotte (Cryopreservation on Isolated Islets, 2nd International Conference on Use of Human Tissues and Organs Search In Transplant, October 1985, pages 46–51).

The devices may be formed as individual droplets which are encapsulated with the aforementioned membrane. The individual droplets, frozen or as macrocapsules, may be conventionally coated in a free fall coating process or suspended from an embedded thread and coated. The cells are thereafter reconstituted, admixed in an appropriate media and may then be implanted by injection into the selected site.

The device 80 may also take the form shown in FIG. 5. More particularly, a rectangular plate 82 is provided with a plurality of through holes 102. The top surface of the plate and the top openings of the holes being coated with poly-para-xylylene coating 104, and establishing the aforementioned membrane. The bottom surface of the plate, and bottom openings of the holes are covered by a poly-para-xylylene coated backing cover 106 which is adhered thereto by a suitable biocompatible adhesive. The interior chambers defined by the side walls of the hole, the membrane and the cover are filled with insulin producing cells within a liquid or gel matrix.

The device of FIG. 5 is preferably manufactured by initially coating plate 82 with poly-para-xylylene so as to provide a continuous conformal coating on all surfaces including the walls defining the openings. The bottom is sealed and the holes filled with distilled water to a level slightly below the top surface. The filled plate is then frozen, and thereafter coated with poly-para-xylylene to the desired membrane thickness. After coating, the device is warmed to thaw, the backing plate removed and the water removed though evaporation. The device is inverted and desired cellular concentration deposited in the holes and onto the membrane. The backing plate is then adhered as mentioned to the bottom surface.

Alternatively, cellular containing media may be frozen within the holes and the plate conformably coated to membrane thickness, and the cells unthawed as described above. In such a device, top and bottom membranes would be provided at each compartment.

Of great importance in the development of a bioartificial pancreases and other biological devices is the ability to: (1) store and inventory the islets for future use; (2) periodically test the islets in inventory to verify and quantify their functionality in order to insure performance specifications in vivo; (3) incorporate the islets into the desired matrix and into the implant device; (4) inventory, test and determine functionality of the devices before implant; and importantly (5) allow adequate time to determine the presence of any latent viral or other pathogenic biologic contaminants to ensure safety for human use. Heretofore, limited success has been reported in maintaining the functionality, in vitro, of pancreatic islets.

These goals are achieved for storage, manufacture, functionality testing inventory, and pathogenic testing by utilizing a matrix based on a hydrogel which has been processed to cleave hydrogen bonds to present a free-flowing, syringable or liquid state around patient body temperature. More particularly, the hydrogel is characterized by a backbone comprised of long chain sequences of amino acids having R-groups whose intramolecular hydrogen bonds can be broken, with resultant uncoiling of the tropocollagen structure. These intramolecular bonds are replaced with hydrogen bonds between hydrogen on the R-groups and water. The hydrogel is supplemented, in the case of a non-collagenase hydrogel, with effective amounts of native collagen and/or boiled or denatured collagen, i.e. gelatin. Either is effective in providing binding site to which the cellular moieties can attach for a stable environment. The collagen based compound acts as a substrate for cellular attachment of islets, hepatocytes or the like, based on thermally dependent hydrogen bond formation and dipole moment interactions, and provides a natural milieu for cellular growth,. The collagen based compound, when boiled, contains polar and non-polar amino acids that readily form a gel based on amine, carboxyl group, hydroxyl group, and sulfhydryl group interactions. The resistance of the matrix to force can be increased by the addition of chelators that remove divalent cation interference from the hydrogen bond and dipole moment interactions. Exposed active groups are used to immobilize water at lower temperatures via this hydrogen bond formation, thus minimizing thermal trauma at lower temperatures.

For storage, an effective amount of a large molecular weight cyroprotectant is added that allows the matrix to be stored at lowered temperatures without cellular damage thereby presenting a condition of suppressed metabolism without the need for cryopreservation. The present invention still further provides a cellular matrix that includes a metabolically stable cryopreservant that provides an inert cushion to thermally dependent cellular expansion and contraction. A preferred cryopreservant is sulfated dextran wherein the sulfhydryl groups provide sites for disulfide linkages and increased matrix resistance to force, as well as inhibiting nitric oxide accumulation. Such sulfated groups also provide sites for growth factors such as IGF-I and IGF-II, known by those skilled in the art to be required for continued islet growth and maintenance.

The storage matrix can benefit by the addition of a divalent chelator, such as citrate, EDTA or EGTA, which can increase the rigidity of the matrix by removing inhibition of —$NH_2$ to —COOH hydrogen bonding, inhibiting deleterious hydroxyl free radical (OH—) formation from superoxide by chelating transition and heavy metals required for this to occur, as well as protecting against contamination thereof. The liquid for constituting the matrix may take the form of a recognized growth media for providing nutrition for the cells. To provide additional protection against microbial contamination, conventional antibiotics can be added.

If the cellular moieties are to be incorporated directly into a device shortly after harvesting, with transplantation taking place without a requirement for storage at lowered temperatures, the cryopreservant may be reduced or omitted. However, for improved transfer across the membrane, it is desirable for the matrix to be substantially in liquid phase at host or patient body temperature. This can be achieved by the divalent chelator amount. It would also be preferable to supplement with growth media, and antibiotics.

Where the matrix and cellular moities are subject to trauma, force or temperature variations during device manufacture, it may be desirable to increase the rigidity of the matrix without affecting the liquification temperature. As described below, this may be achieved by enhancing bond formation through the use of amino acids with —R groups of differing hydrogen bond formation potential.

Such amino acids and related compounds provide cellular protection from nitric oxide and its metabolites, which are known to cause cellular death from nuclear destruction and other related injuries. The cellular matrix utilizes these amino acids and related compounds to inhibit L-arginine from forming nitric oxide through any of the isoforms of nitric oxide synthase. Cysteine, in particular, and other related compounds with sulfhydryl groups that are found in collagenous material also serve to scavenge already formed nitric oxide and thereby prevent nitric oxide induced damage.

The present invention utilizes the new hydrogel matrix, for purposes of a bioartificial pancreas, wherein isolated porcine islets can be stored for extended periods, six months and longer, at subambient temperatures, such as refrigerator temperatures, 4° C. As discussed above, the improved hydrogel matrix is based on heated or otherwise denatured animal collagen that is protective against lowered temperature conditions by an inert polymeric buffer substrate such as dextran, amylopectin, proteoglycans and like large molecular weight cryoprotectant. As will be appreciated by those skilled in the art, the improved hydrogel matrix is based on the breaking of covalent chemical bonds by boiling or chemical treatment, and increasing the number of heat sensitive hydrogen bonds and dipole moment attractions. By replacing the covalent chemical bonds with such temperature sensitive bonds and attractions, the desired tissue can be embedded in a solid matrix formulation at colder temperatures for sustained storage. By keeping the desired tissue in a more solid matrix, damage resulting form constant exposure to water is reduced, and metabolism and gas exchange are suppressed. In effect, the invention preserves the tissue without going to the extreme of sub-zero cryopreservation techniques. This matrix can then be made liquid at desired higher temperatures to increase metabolism and growth, as well as to facilitate diffusion of nutrients and hormonal products. Because the original hydrogel substrate had its intermolecular covalent linkages broken (such as sulfhydral linkages), the matrix can then be modified according to desired specifications by addition of moieties that increase dipole moment attractions or hydrogen bonding.

Many examples of hydrogel substrates, in addition to gelatin, are available that are suitable for this process; including boiled agarose, alginate, keratin and other amino acids, amino glycans and proteo glycans and other gels having a constituent backbone comprised of long chain sequences of amino acids having R-groups whose intramolecular hydrogen bonds can be broken and replaced with hydrogen bonds between hydrogen on the R-groups and water, thus yielding a well recognized gelatinous consistency. In this connection, by way of example, 20 grams of agar were placed in 5 ml of Media 199 and the resulting solution reduced to a pH of 2 with HCl 1 N. The solution was held at 37° C. and stirred for 10 minutes until dissolved. To the solution, 100 mg of dextran was added and a millimolar concentration of EDTA. The resultant formulation was liquid at recipient temperature and substantially more viscous at 4° C. refrigerator temperature. Such techniques can also be employed for the other described hydrogels, adjusting the additives as required to achieve the desired objectives.

Depending on the desired physical properties, these substrates can have their resistance to force (firmness) increased or decreased by addition of other chemicals. As described in the example below, such firmness is increased by addition of amino acid moieties with polar R groups or accessible hydrogen/hydroxyl groups to increase dipole moment attractions and hydrogen bonds as the enhanced substrate cools. The addition of essentially intact collagen or denatured collagen, gelatin, to any of the above hydrogel substrates provides a lattice structure for tissue or isolated cells to anchor. Thus, any tissue can be embedded in this type of hydrogel matrix, and its properties adjusted, depending on the desired performance of the isolated tissue as described in the example below.

For the purpose of protecting and preserving isolated pancreatic islets, one example uses heated animal collagen, i.e., gelatin, and protects the living tissue against lowered temperature conditions with an effective amount of an inert polymeric buffer substrate such as dextran, amylopectin, proteoglycans, or other large molecular weight cryopreservants able to limit trauma induced by thermal changes in water. These substrates act as a buffer against thermal expansion and contraction. Without such a buffer, the islets have diminished capacity to survive the physical trauma induced by the expansion and contraction caused by the temperature changes, as well as trauma induced to cell membranes as a result of heat-sensitive movement of water.

In addition, the improved hydrogel matrix protects such tissue against harsh barometric trauma such as vacuum pressures encountered during polymeric coating procedures. This is achieved by increasing the gelatin's resistance to force through modulation of temperature and substrate dependent hydrogen and disulfide bonds. The matrix for storage and manufacture may be strengthened by enhancing hydrogen bond formation by addition of amino acids containing carboxyl or amine R-groups (as found in glutamic acid or arginine), disulfide linkages by addition of cysteine or methionine residues, or increased dipole moment attractions by addition of amino acids with non-charged but polar R groups such as glutamine, threonine, or asparagine. The hydrogen bonds and dipole moment attractions can be further increased with a divalent chelator such as EDTA which also provides protection against matrix bacterial contamination during storage.

Collagen is found in all animal tissues as repeating tropocollagen polypeptide subunits comprised of amino acids not usually found in other proteins including glycine, hydroxyproline, and hydroxyzine. Collagen forms insoluble fibers with high tensile strength when covalent cross links are formed with mature tissue. However when collagen is boiled as in the process for making conventional gelatin, these cross links are broken, and its three dimensional structure is unfolded, yielding a multitude of polypeptides with loose association.

Collagen is the major connective protein found in a variety of tissues including, in order of increasing rigidity, ligaments, tendons, cartilage, bone and teeth, indicating the ability of collagen to attain a wide array of physical properties based on the intra- and inter-molecular bonding forces. Intact tropocollagen is the longest known protein, being 3,000 Angstroms in length, but only 15 Angstroms in diameter. Boiling collagen breaks the insoluble tightly coiled helical tropocollagen subunits enabling the insoluble tropocollagen molecule to open up from its original tightly coiled cable conformation, into three separate peptide chains. The individual peptide chains are then used to perform two vital functions for the embedded islets. First, they provide binding sites for the isolated islet tissue to attach, and second, they provide a temperature sensitive substrate to be used for protection of the islets during the coating process described above.

The loss of the tightly coiled triple stranded helical structure indicates that the strand is stabilized by a summation of weak, individual interactions that collectively reinforce each other via cooperative interactions. Boiling causes the individual strands to uncoil, thus making their side chain R-groups available for other interactions. The boiled collagen exposes multiple binding areas for the islets to attach. FIG. 6 is an electron micrograph (3,000 magnification) of isolated islets binding to one of the open single peptide strands that once comprised a tightly coiled tropocollagen helix. An incompletely uncoiled helix is still present in the boxed area of FIG. 7, also indicating the native material may be used as a supplement for increasing the binding sites.

Breaking the transverse hydrogen bonds that bind the individual collagen strands to each other overcomes the steric stability contributed by the repulsion of the pyrrolidone rings of the hydroxyproline and proline residues. As a result, when enough of the interstrand hydrogen bonds are broken, the steric repulsion destabilizes the superhelical coil, thus opening up the individual strands. By adding supplemental amino acids that contain highly charged polar groups, such as glutamic acid and arginine, increased hydrogen bond formation to surrounding gelatin strands result, thus attracting and immobilizing water and polar groups on other gelatin strands at temperatures below 30° C. This immobilization of water reduces cell membrane damage from temperature changes. The addition of cysteine allows strong disulfide cross-links to be formed. Other amino acids that increase these kinds of bond formation include those with polar side groups, both charged and uncharged, and those with ability to form sulfide linkages.

By increasing the number of hydrogen bonds, and increasing disulfide bond formation, the matrix is more resistant to force at temperature below 30° C. Intact porcine skin collagen has a thermal stability constant of 65° C., the temperature at which 50% of the tropocollagen strands disassociate. By breaking the helical structure, the melting temperature of the gelatin based matrix is lowered to about 30° C. This is critical for allowing the matrix to be suitably liquid at body temperature (37° C.) to allow fast, physiologic transfer of glucose and other nutrients across the para-xylene membrane.

Removal of divalent cations that interfere with hydrogen bond formation improves resistance to force, i.e. rigidity of the matrix. This can be accomplished by addition of a wide number of chelators such as EDTA, EGTA, citrate and like divalent cation chelators. The resultant increase in matrix rigidity provides protection against conditions experienced by the matrix tissue during the polymer coating process, vacuum pressure and low temperature, which could in some instances adversely affect the islets.

In order to increase islet binding, porcine intact collagen may be added in small amounts to provide additional binding network for the porcine islets. As discussed above, the matrix for storage and manufacture may be strengthened by enhancing hydrogen bonding and amine to carboxyl cross-linking with a divalent chelator such as EDTA, such chelators also providing protection against matrix contamination during storage. In order to provide maximum diffusion across the membrane in vivo, the matrix is designed to be in a free flowing, syringable or liquid phase at recipient body temperature while being in solid phase at the lowered storage temperatures, preferably slightly below patient temperature, i.e. 35° C. and at storage temperature. Inasmuch as the islets have reduced metabolism at lowered temperatures and the membrane coating process may take place at that temperature or thereabove, generally at ambient temperature, it is preferred to maintain the aforementioned matrix slightly below patient temperature for coating.

The gelatin, for use with porcine islets, preferably a porcine based gelatin, is admixed with a liquid, preferably one of the conventional biological growth media. Based on the desired gel temperature, the gelatin is present at about 0.01 to 30 mM concentration, generally 0.1 to 10 mM concentration, and preferably in the range of about 0.5 to 5 mM concentration, all providing a solid phase at storage temperature and a liquid phase at transplant temperature. The liquid, water or substantially inactive fluids and preferably at least in part a growth media is present generally in the range of 15 to 96.5 weight percent of matrix, and preferably in the amount of about 45 to 84.5 weight percent of matrix. The buffer substrate is present in the gelatin and liquid matrix in an amount sufficient to provide thermal protection at the selected storage temperature, in the amount of 0.01 to 1000 micromolar concentration, generally in the range of about 0.5 to 500 micromolar concentration, and preferably in the range of 10 to 100 micromolar concentration in the matrix. The divalent chelator may be present in the storage matrix to provide the desired structural integrity, generally in the range of about 0 to 100 mM concentration, and preferably in the range of about 0.05 to 10 mM concentration in the matrix. The protein media may be present in the matrix to provide nutrition for the islets in an amount of 0.0 to 30.0 weight percent of matrix, generally in the range of about 0.05 to 20 weight percent of matrix and preferably in the range of 5 to 15 weight percent of matrix. The antibiotic are present to prevent infection or contamination in conventional biological packages in the amount of 0.0 to 30 weight percent of matrix, generally in the range of 0.05 to 10 weight percent of matrix, and preferably in the range of 1 to 6 weight percent of matrix. The native collagen may be present in the range of about 0 to 1000 micromolar concentration, generally in the range of about 1 to 100 micromolar concentration, and preferably in the range of about 5 to 50 micromolar concentration in the matrix. The amino acids are present in the amount of 0 to 300 mM concentration.

EXAMPLE 5

Depending on the requirements desired of the matrix to force resistance, a wide range of concentrations of additives exist for either storage of tissue, culture tissue, or coating of tissue with the conformal polymer described above. A suitable matrix may be prepared in accordance the foregoing using the following matrix base for storage, manufacture and implantation:

cryopreservant 0.01 to 1000 micro molar Dextran, 500,000 MW, Sigma Chemical Co., St. Louis Mo., Cat No. D5251
gelatin 0.001 to 100 mM gelatin from porcine derived collagen, approximate bloom 5–300, Sigma Chemical Co., St Louis Mo.
protein additive 0 to 30% newborn calf serum, Life Technologies, Gaithersburg Md., Cat. No. 16010-43
antibiotics 0.1 to 30% penicillin-streptomycin solution, Irvine Scientific, Santa Ana Calif. Cat. No. 9366 .001 to 30% fungizone, Irvine Scientific, Santa Ana Calif., Cat. No. 9352 0.001 to 30% Collistin 0.001 to 30% Ceftazidime
collagen 0.01 micromolar to 30 mM Type II, acid soluble from calf skin, Sigma Chemical Co.,St. Louis Mo., Cat. No. 3511
amino acids 0.01 micromolar to 300 mM dl-cysteine hydrochloride, Sigma Chemical Co., St. Louis Mo., Cat. No. 9768 0.01 micromolar to 300 mM L-glutamine, Sigma Chemical Co., St. Louis Mo., Cat. No. G-7029 0.01 micromolar to 300 mM dl-arginine hydrochloride, Sigma Chemical Co., St. Louis Mo., Cat No. A.-4881 0.01 micromolar to 300 mM l-cysteine hydrochloride, Sigma Chemical Co., St. Louis Mo., Cat. No. C-4820 0.01 to 10 mM l-glutamic acid hydrochloride, Sigma Chemical Co., St. Louis Mo., Cat No. G-2128
divalent chelator 0.001 mM to 100 mM EDTA
growth media Appropriate volumes to bring other constituents to desired concentrations, Media 199, Sigma Chemical Co., St. Louis Mo., Cat. No. 12340-022

In the present invention, these conditions of a stable, firm collagen infrastructure are recreated by placing the islets in a matrix comprising boiled denatured collagen, preferably in the presence of the aforementioned buffer substrate and also in the presence of a divalent or calcium chelator such as EDTA, EGTA, citrate or the like. This matrix allows the islets to again attach to a collagenous medium wherein the properties of the matrix may be controlled to provide a liquid phase at body temperature. Furthermore, the matrix resistance to force can be controlled through the divalent chelator to provide a solid phase at the coating temperature experienced in the coating cycle for applying the membrane. The solid coating phase, enhanced by the thermal protection of the cyropreservant provides protection from barotrauma that would otherwise be experienced at the coating vacuum. Moreover, this matrix enhances islet viability in vitro, allowing testing of the islet tissue prior to applying the membrane, and thereafter prior to any implantation. Prior to the above matrix, the generally reported and accepted survival of islets by those skilled in art was in the range of 7–14 days. As discussed in greater detail below, islets in the present matrix have survived in vitro without diminished functionality for periods in excess of 174 days.

The collagen containing media may be denatured collagen or essentially intact collagen. A suitable denatured collagen is a conventionally derived boiled gelatin from animal, avian, fish and human sources. For instance, food grade gelatin may be used as well as medical grade boiled collagens, all processed so as to an unfolded fibrous structure wherein the native collagen three dimensional structure is unfolded and the resultant collagen yielding polypeptides in loose association. The gelatin may be supplemented with essentially intact animal collagen to provide native collagenous binding structures. The collagen is present in sufficient amount to provide the desired structural rigidity in a three dimensional matrix and for providing attachment sites for the islets therewithin. The buffer substrate for protecting the islets at lowered temperature, i.e. preferably dextran at 500,000 mw, preferably sulfated which will contribute to increasing hydrogen bond formation because of the sulfate side groups. Others include amylopectin. The growth media may be a tissue culture media such as Medium 199, RPMI and the like. The protein medium may be any sera derived from human or animal sources, preferred sera by way of example being newborn calf serum or fetal pig sera.

In a series of experiments which measured the same matrix ingredients with the exception of one having less than 1% Dextran, while the other had greater than 7% dextran, the ability of the embedded islets to secrete insulin in response to a 100 mg/dl glucose challenge doubled in the matrix with greater dextran, while the islets in matrix with little to no dextran had their insulin secretory abilities halved over the same time period.

EXAMPLE 6

Islets were isolated from the splenic lobe of fresh porcine pancreases using conventional collagenase digestion and Ficoll separation. The islets were then incubated in Media 199 at 37° C. for 5 days. The islets were transferred to a hydrogel matrix comprising a collagen containing medium, a buffer substrate, a growth media, a protein media, and a divalent chelator. The matrix also contained various conventional additives such as antibiotics and bacteriostatics. The matrix is solid at around room temperature while presenting a liquid phase at patient temperature, around 37° C.

EXAMPLE 7

A suitable matrix may be prepared in accordance with the foregoing using the following as a matrix base for storage, manufacture and implantation:
cyropreservant 6.0 grams Dextran, 500,00 mwt., Sigma Chemical Co., St. Louis, Mo., Cat. No. D-5251
gelatin 14.5 grams Knox unflavored gelatin, Knox Gelatin Inc., Englewood Cliffs, N.J.
growth media 60 ml. Medium 199, Sigma Chemical Co., St. Louis, Mo., Cat No. 12340-022
protein media 0–15% Newborn calf serum, Life Technologies, Gaithersburg, Md., Cat. No. 16010-043
antibiotics 1–3% Pennicillin-Streptomycin Solution, Irvine Scientific, Santa Ana, Calif., Cat. No. 9366 1–3% Fungizone, Irvine Scientific, Santa Ana, Calif., Cat. No. 9352
collagen 50–100 mg Type II, acid soluble from calf skin, Sigma Chemical Co., St. Louis Mo., Cat. No. C-3511

To formulate the matrix base, the growth media is placed in a beaker and with a stirring bar is spun rapidly while heating on a stir/heat plate until well mixed. The buffer substrate is slowly added to the growth media while maintaining stirring. The combined solution is sonicated for 1–2 minutes after which the gelatin is slowly added to the solution while stirring and heating. Thereafter, the solution is microwaved for five 10 second intervals and then sonicated for 1–2 minutes. Then, 2–10 mM of EDTA is added to the warm solution, thoroughly mixed and placed in a 60°–70° C. heated/vacuum drying oven and evacuated. The heated, evacuated solution is equilibrated for at least five minutes and cooled to 37° C. before adding islets.

EXAMPLE 8

Islets were added to the matrix of Example 6 above at a rate of about 200 islets/100 ul of matrix. A portion of the islet matrix was transferred to 36 mm polystyrene wells. The remainder of the islet matrix was transferred to an eighteen 6.5 mm. open ended cylinder device at the rate of 220 islets/10 ml of matrix. The device was cooled to solidify the matrix and conformally coated with about 4,000 Angstroms of poly-para-xylylene N.

The islets in the wells and the devices were stored in a refrigerator for periods of up to two weeks before being brought to 37° C. for periods of one to three hours during which time static incubations were performed at varying glucose concentrations.

The islets in the wells had the surrounding nutrient medium changed every thirty days. Incubation for 15 minutes in 22.0 mM glucose stimulated 3 uU insulin at 73 days post isolation. The device secreted 1.61 uU, 6.67 uU, 15.6 uU insulin in response to static incubations of 2.25, 5.5, and 11.0 mM glucose for 180 minutes at 36 days post isolation. Islet structure remained grossly intact in all islets for 73 days without bacterial contamination.

Figure 8:
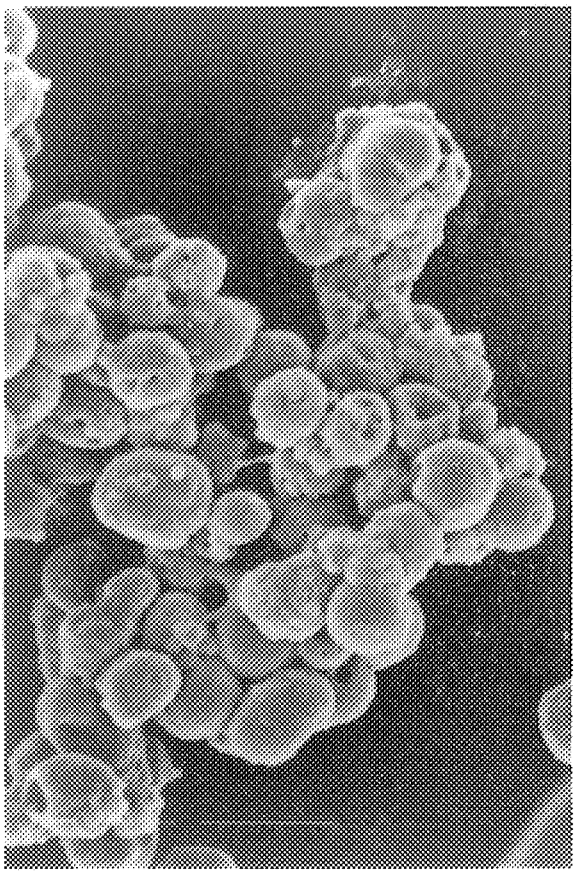
FIG. 8 is an enlarged view of a portion of FIG. 7 showing an unattached cluster of islets.
Figure 7:
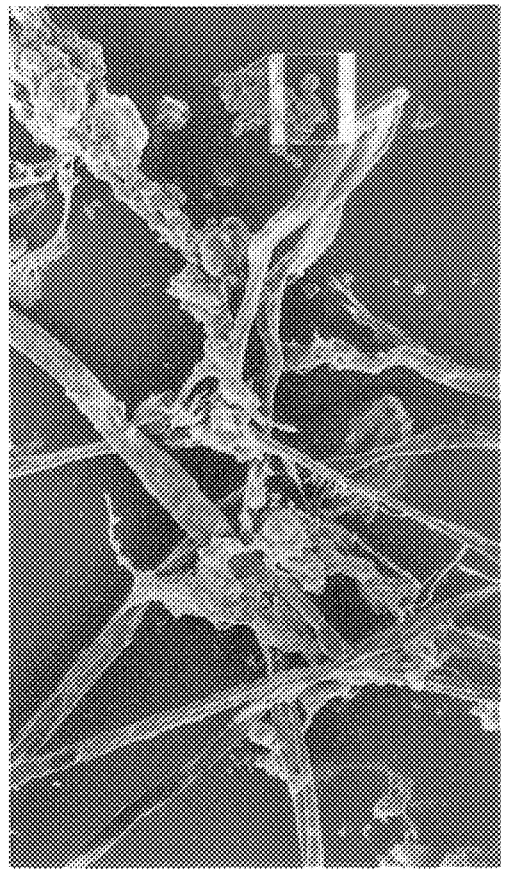
FIG. 7 is an enlarged view of a portion of FIG. 6 illustrating attached and unattached clusters of islets in the matrix.
Figure 9:
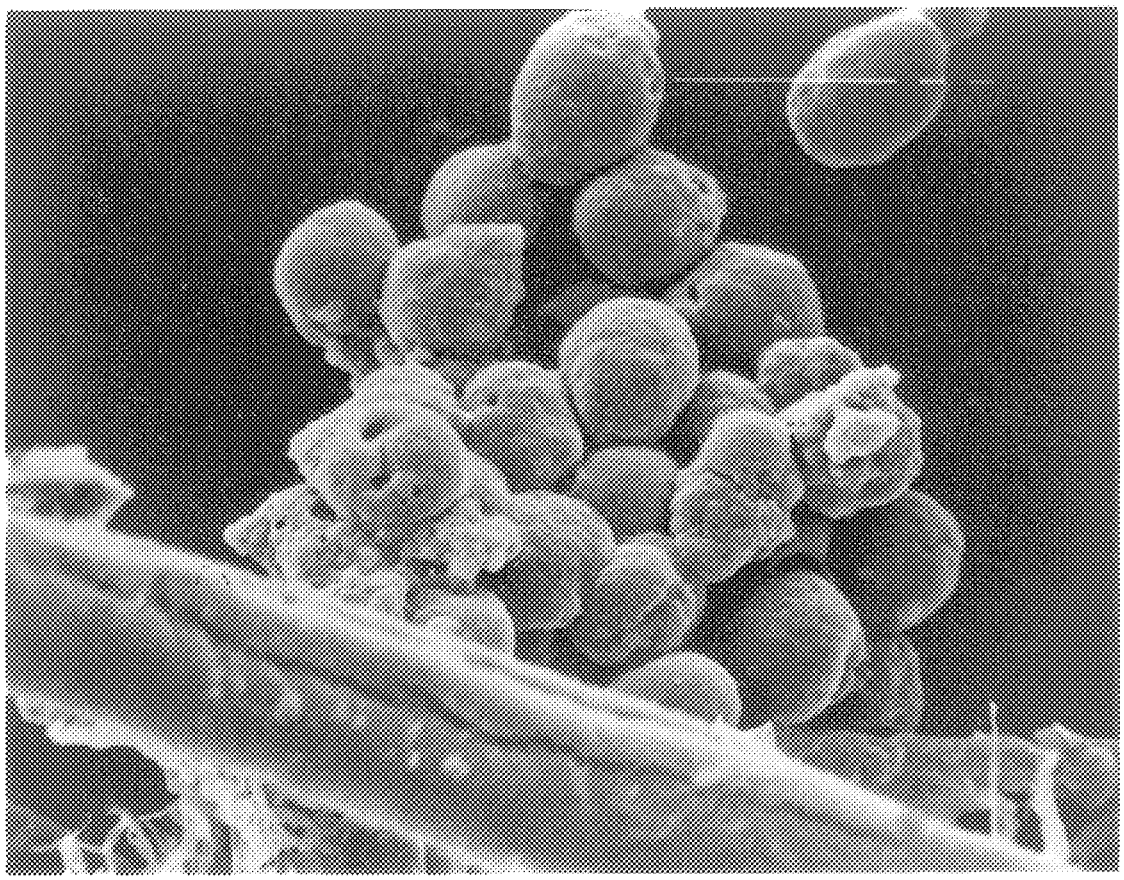
FIG. 9 is similar to FIG. 8 showing an attached cluster of islets.
Figure 10A:
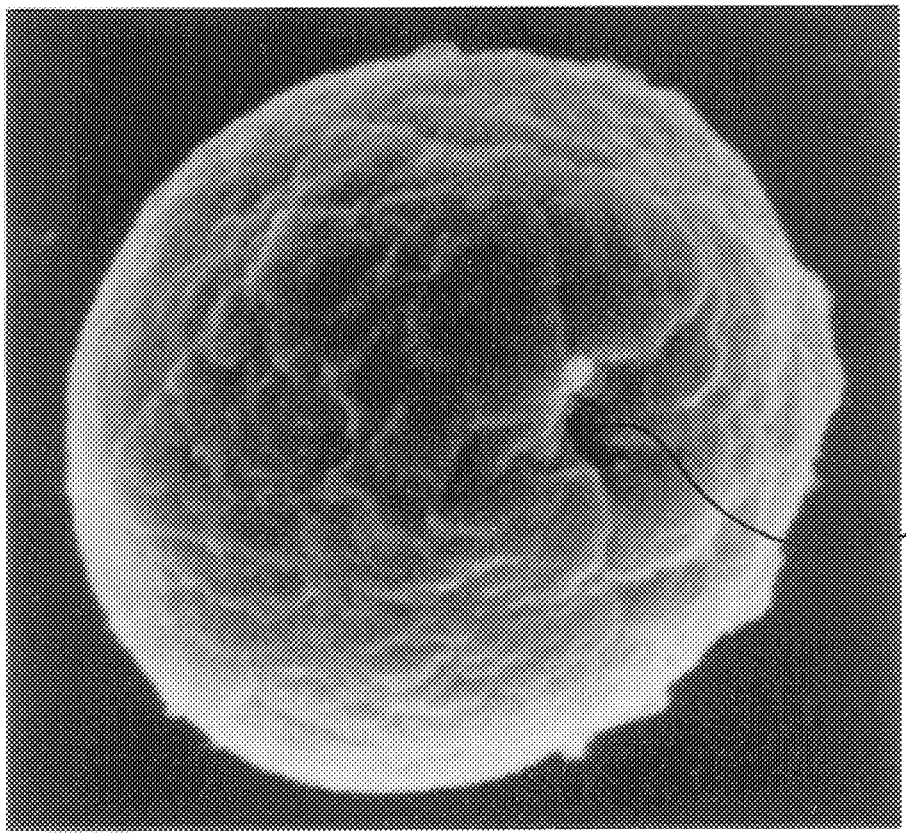
FIG. 10A is a view similar to FIG. 6 of a single islet include a binding site for attachment to the fibers, and 10B is a view of a single islet undergoing cellular division.
Figure 10B:
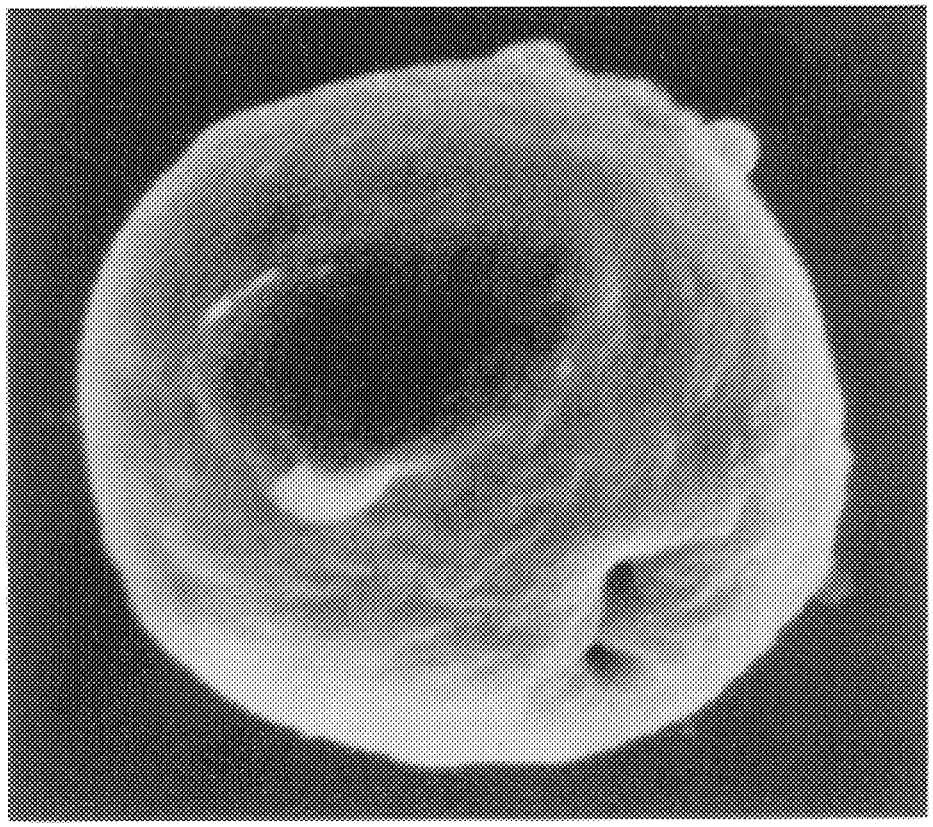
Figure 12:
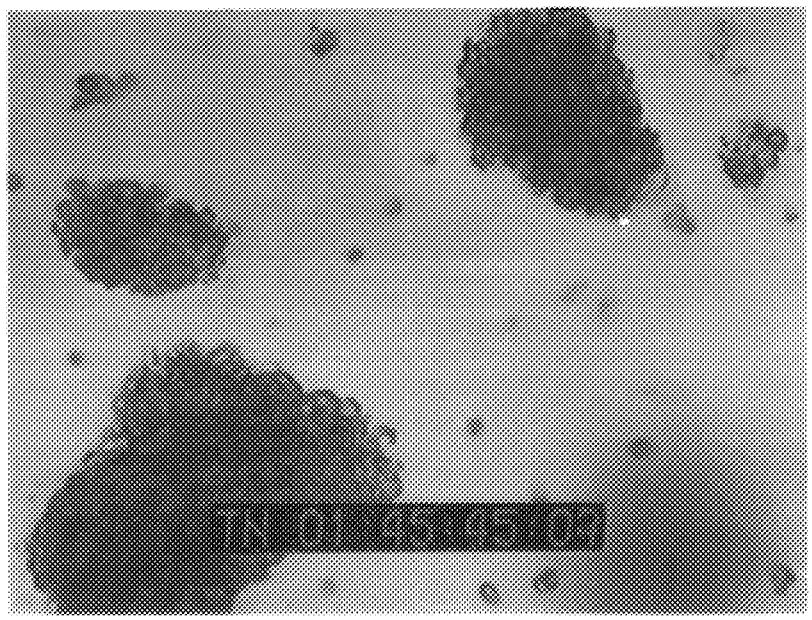
FIGS. 12 and 13 are light microscopy photographs of islets following removal from the matrix.
Figure 13:
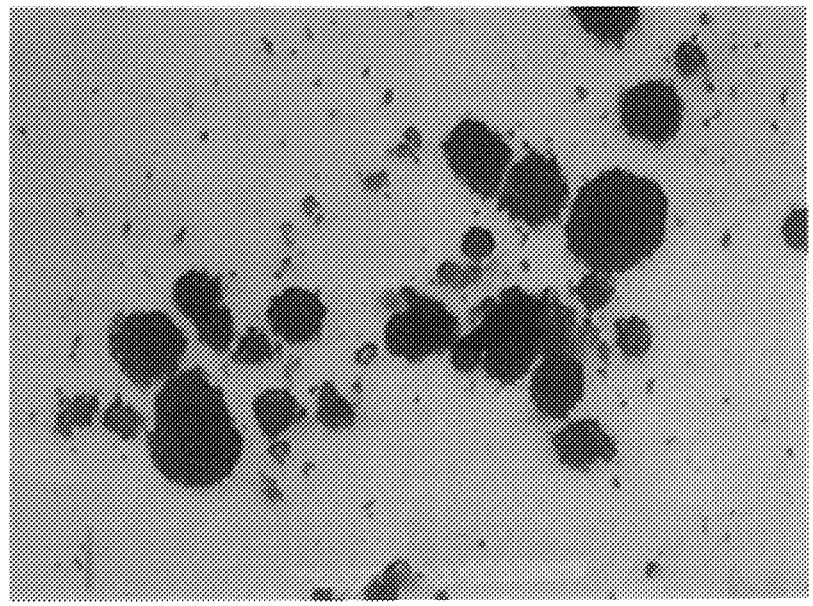

FIG. 6–11 illustrate scanning electron micrographs (45–18,000×) of 90 day old islets. As shown in FIG. 6, clusters of islets representively indicated by numeral 200, are attached to the collagen fibers 202 (45×) at various locations along the length thereof demonstrating the adherence of the islet tissue the matrix polymers, with maintenance of islet gross structures. FIG. 7 is a further magnification of FIG. 6 illustrating the attachment of islets along the collagen fibers (3,000×) with inset of FIG. 7 as shown in FIG. 8 being a cluster of islets not yet attached to the fibers. FIG. 9 shows a representative cluster of islets attached to the fiber network (9,000×). FIG. 10A shows the binding site 204 of a single beta cell (18,000×) for attachment to the collagenous fibers. FIG. 10B shows a single beta cell showing indications of cellular division in the matrix. FIG. 11 shows a strand of collagen 206 that was not unfolded during boiling. FIGS. 12 and 13 are light microscopies of 90 day old islets after removal from the matrix by addition of divalent cations (4mm calcium chloride) and reveal grossly intact morphology.

Currently accepted techniques for islet harvesting rely on highly purified intact whole islets for transplantation. The time and materials required to achieve this result are lengthy and costly, generally with low yields. Heretofore, when the pancreas was overdigested resulting in substantial islet fragmentation, the harvest was aborted inasmuch as it was conventionally not accepted that fragmented islets retained functionality. The above described matrix permits the use of such fragmented islets with intact functionality in conventional storage media or matrices.

The present invention also permits overdigested pancreata to be utilized in the aforementioned matrix. More particularly, a porcine pancreas was conventionally digested by the collagenase method. Rather than terminating the digestion when free floating whole islets were observed, the digestion continued until substantial fragmentation was observed. Thereafter, the digestion was terminated, the fragments repeatedly washed and centrifuged until a pellet of fragmented islets substantially free of acinar tissue was observed. The islets were mixed with the matrix formulation of Example 7 above at a rate of about 3,000 islet equivalents/ml of matrix. The islet matrix was then deposited in a 36 mm plate well and refrigerated. Daily, the islet matrix was heated to 37° C. and observed under a microscope and video taped. At the initial days, each field of view revealed substantial free floating islet fragments. In passing days however, the fragments abated and clusters of apparent whole islets appeared. At day 14 post harvesting only clusters of islets, substantially free of fragmentation were apparent, with insulin levels of 150 uU/ml released in response to 100 mg. glucose stimulations.

The above matrix also provides beneficial results with cryopreserved islets, frozen for eighteen months in liquid nitrogen, which have heretofore demonstrated poor functionality upon reconstitution. Islets which had been cyropreserved were thawed and admixed in the above matrix at 1,000 islets per 100 ul of matrix and distributed and solidified in a device having eight open-ended cylinders. The device was then conformally coated with about 4,000 Angstroms of poly-para-xylylene N. Maximal secretion from the device two days after coating was 2.2 uU/ml. Every 3–4 days thereafter, the maximal secretion approximately doubled to 4.4, 8.3, 19.0 and 33.0 uU/ml in response to exposure to normal blood glucose concentration of 100 mg. Inasmuch as the average fasting serum insulin concentration in a non-diabetic subject ranges from 5–20 uU/ml, it is apparent the cryopreserved islets after thawing provided therapeutic functionality.

The matrix when used exteriorly of the device in vivo also promotes vascularization and lipid formation adjacent the membrane at intramuscular transplantation sites which heretofore have not been highly regarded as providing sufficient oxygenation and vascular access to promote islet longevity. More specifically, about 32 coated open-ended cylinders of FIG. 5 were implanted intramuscularly in a 15 kg. adult beagle between latissimus dorsi muscles. Other sites include readily accessible areas such as subcutaneous fat, intraperitoneal locations, or locations near the portal circulation. The surgical site after insertion of the devices was filled with about 20 ml. of matrix. The cylinders in aggregate contained about 30,000 islets. The dog was pancreatectomized and monitored for blood glucose levels and porcine C-peptide levels. Positive contributions of the device to glucose levels and C-peptide levels were noted, however at Day 17, severe organ malfunction resulting from the pancreatectomy was noted and the animal was sacrificed. Upon removal of the devices, pathological examination revealed substantial microvascular formation and lipid growth in the matrix overlying the membranes, both of which are indicia of requisites for islet maintenance and longevity.

Figure 14:
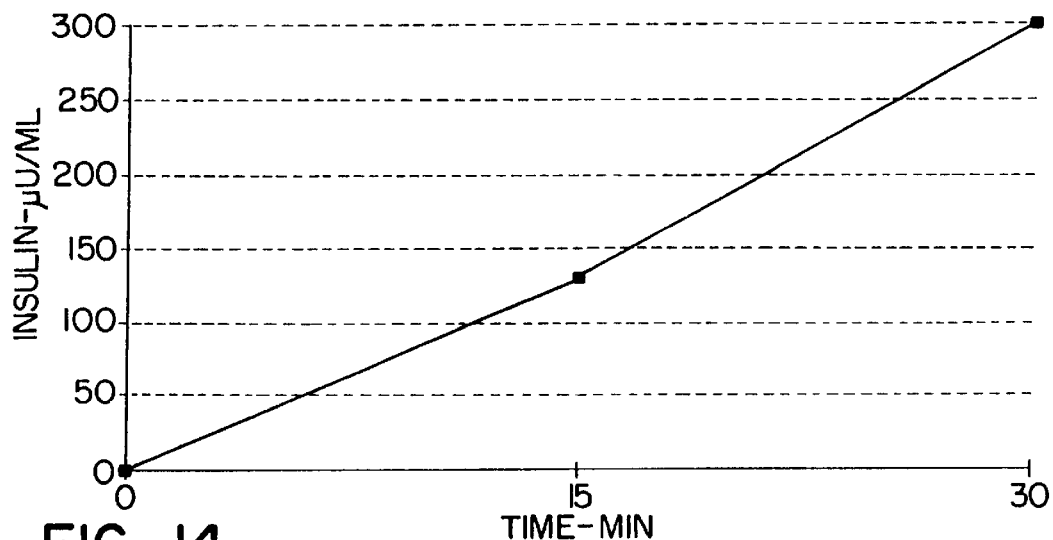
FIG. 14 is an insulin versus time graph in response to a 100 mg/dl glucose challenge in-vivo for a device in accordance with the present invention.
Figure 15:
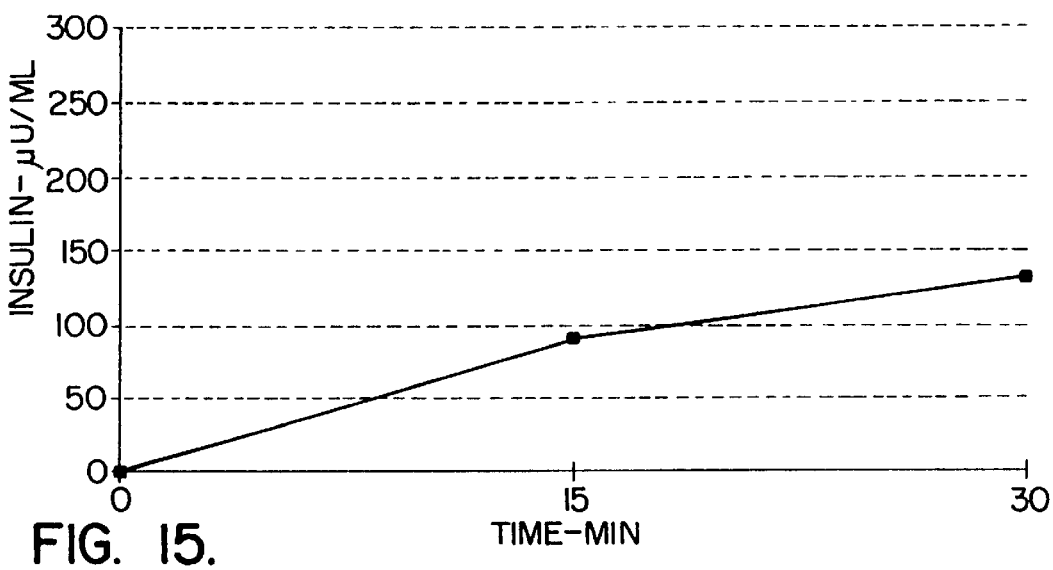
FIG. 15 is an insulin versus time graph in response to a 50 mg/dl glucose challenge in-vivo for the device of FIG. 14.

The matrix in combination with the membrane also releases insulin within recognized time frames in response to glucose challenge and ceases release after removal of challenge, indicative of rapid transmission of glucose signal to the islets to stimulate insulin release, and diffusion of released insulin across the membrane when the signal is removed. Moreover, an inability of the device to turn off quickly after normalization of glucose levels could result in continued production of insulin after normalization and result in potentionally threatening hypoglycemic conditions. The ability of the present device is clearly demonstrated by the following. Therein, matrix was embedded in an eighteen cylinder device which was conformally coated with about 4,000 Angstroms of poly-para-xylylene N. The devices were tested on days 3, 8 and 12 thereafter. As shown in FIG. 14, in response to exposure to 100 mg/dl glucose, the devices exhibited increased insulin production within 15 minutes of stimulus and reached a peak of 300 uU/ml of insulin. The devices were removed and placed in a 50 mg/dl glucose solution and as shown in FIG. 15 reached a peak of 130 uU/ml of insulin, substantially reduced in comparison with the foregoing. Further testing determined that insulin production returned to dormant levels within 10–20 minutes. Additionally, the devices were placed in a 400 mg/dl glucose exposure. Therein, the trends of stimulus and shut off were similar. Moreover there was no apparent diminution in islet secretion in response to glucose over the test period demonstrating that the islets are able maintain and improve their functionality within the coated device.

EXAMPLE 9

Figure 16:
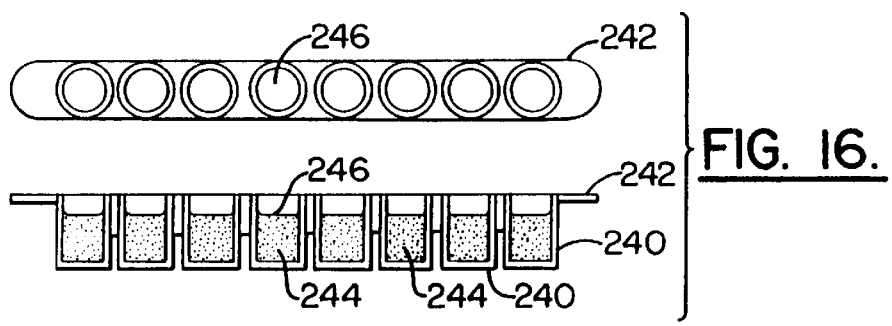
FIG. 16 is a side elevational view of another embodiment of a device in accordance with the present invention.

A suitable device for containing the cellular matrix is an eight well polyethylene strip available from CoStar Inc., Cambridge, Mass. providing a plurality of islet containing capsules. As shown in FIG. 16, each capsule or well 240 of the strip 242 was injected with about 20 dl of matrix 244. Each strip contained about 30,000 to 100,000 islets substantially evenly distributed among the wells. The upper surface of the matrix is recessed beneath the top surface of the strip. The strips and the upper surface of the matrix are conformally coated with poly-para-xylylene N to a thickness of about 4,000 Angstroms. The recessed matrix provides a membrane surface 246 which is thus protected against direct tissue contact in implantation. Further, any fluid forces generated by the recipient result in only compressive forces on the membrane and matrix thereby lessening the potential for membrane tearing or rupture.

Figure 17:
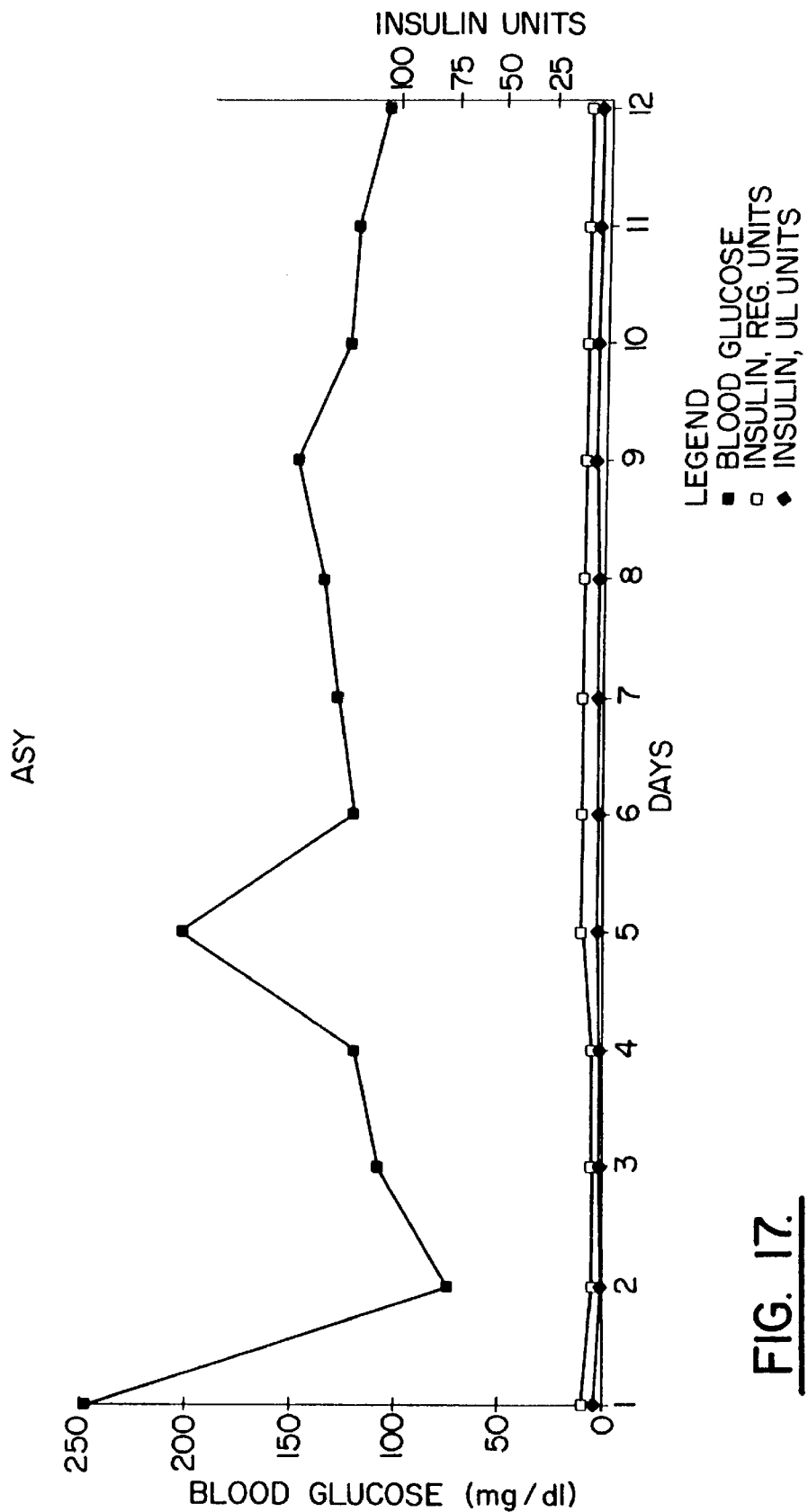
FIG. 17 is a blood glucose versus days for a diabetic dog implanted with the devices shown in FIG. 16.

A first dog, Dog ASY, a 9 kg. purpose bred female Beagle had the equivalent of three strips containing about 30,000 islets inserted through an incision intramuscularly along the left dorsal thorax behind the shoulder. Thereafter, the incision is infiltrated with about 20 ml. of non-cellular matrix and the incision closed. Seven days later Dog ASY received a complete pancreatectomy. Blood Glucoses were determined daily using a OneTouch Meter manufactured by Lifescan, as well as by standard clinical automated chemistry machines. The daily fasting blood glucose readings are shown in FIG. 17. In order to keep the blood glucose level below about 150 mg/dl, Dog ASY received a combination of human Ultra-Lente insulin and regular insulin in the noted total amount and substantially equally divided with respect thereto, the regular insulin being administered to control blood glucose levels and the Ultra-Lente being administered to maintain glucose levels, all in accordance with conventional practice. The number of islets in the devices is well below the number estimated by other researchers for glycemic control, about 8,000 islets per kg or about 120,000 islets for a dog of the subject's size.

In view of the islets deficit, it is nonetheless important to determine that the device is functioning within the recipient. This may be accomplished by determining the C-peptide levels through porcine-specific radioimmune assay (RIA) .

Figure 19:
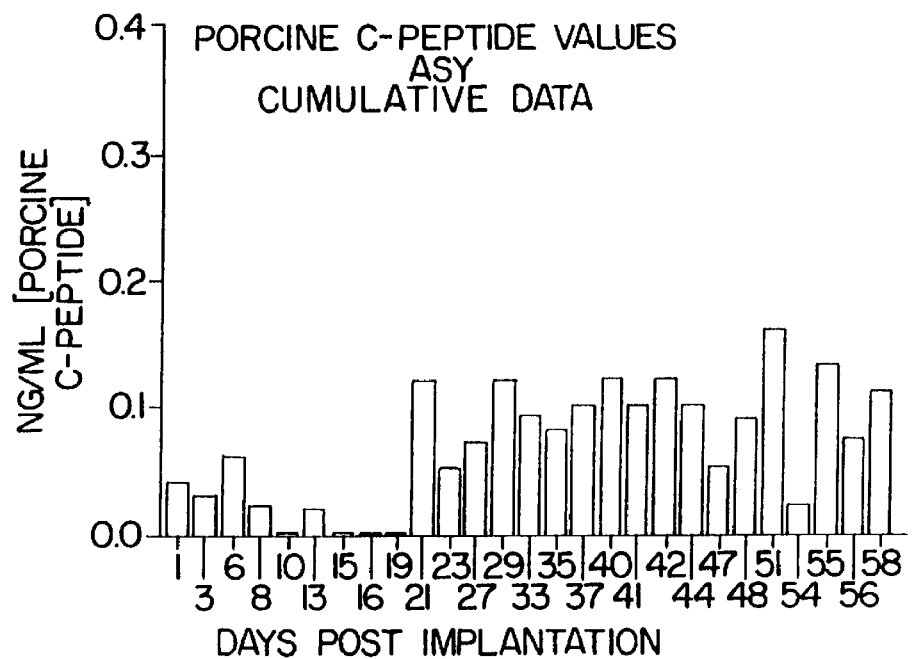
FIG. 19 is a porcine C-peptide versus days post transplant for the dog of FIG. 17.

This assay measures, a "C" shaped peptide that is cleaved off the proinsulin molecule by peptidases before it leaves the islet, resulting in the bioactive insulin molecule. C-peptide is species specific. Highly specific RIA kits, available from Linco, Inc. Of St. Louis Mo., readily distinguish between canine C-peptide and porcine C-peptide, a detection of the latter of which is indicative of insulin production by the implanted devices. For Dog ASY blood samples were periodically collected and assayed for porcine C-peptide and the results are depicted in FIG. 19. Therein, the devices were implanted on Day 1 and the pancreas removed on Day 8. During the period before the pancreas was removed, porcine C-peptide was detected in the blood samples indicating the device was producing porcine insulin. Throughout the trial, detectable levels were determined except for apparent quiescent periods.

Figure 18A:
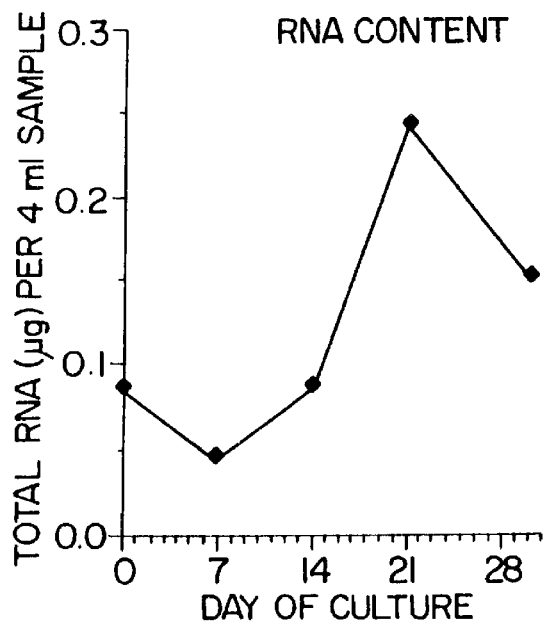
FIG. 18 is islet RNA content, insulin secretion, and viable islet number as a function of time in matrix culture.
Figure 18B:
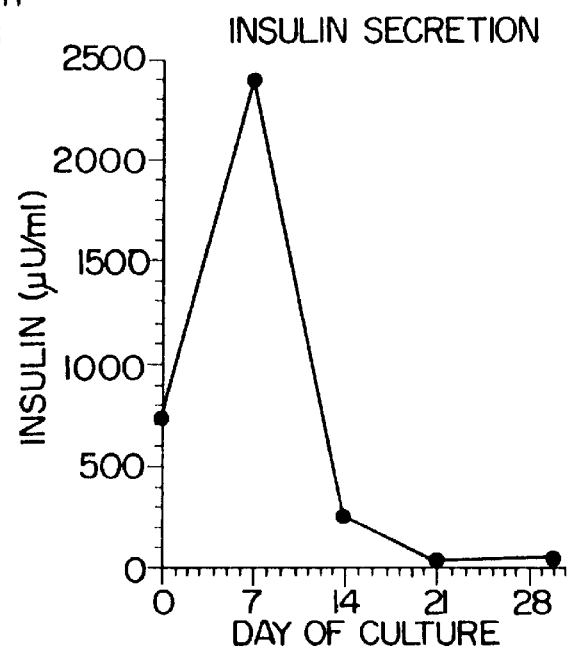
Figure 18C:
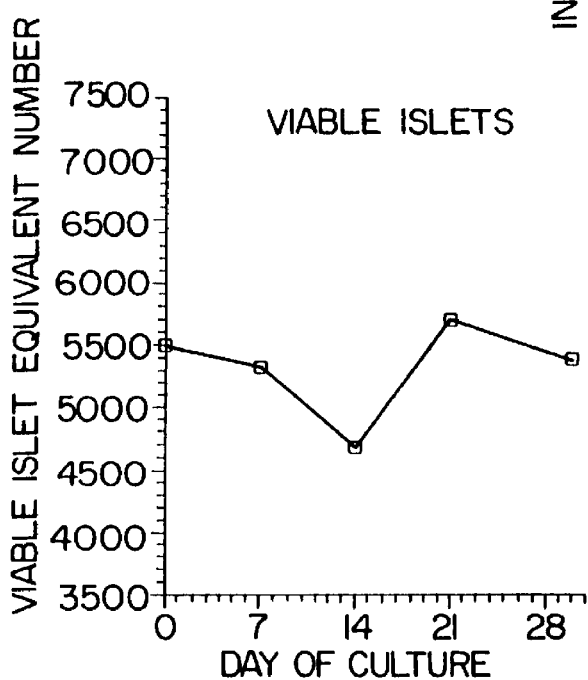
Figure 20:
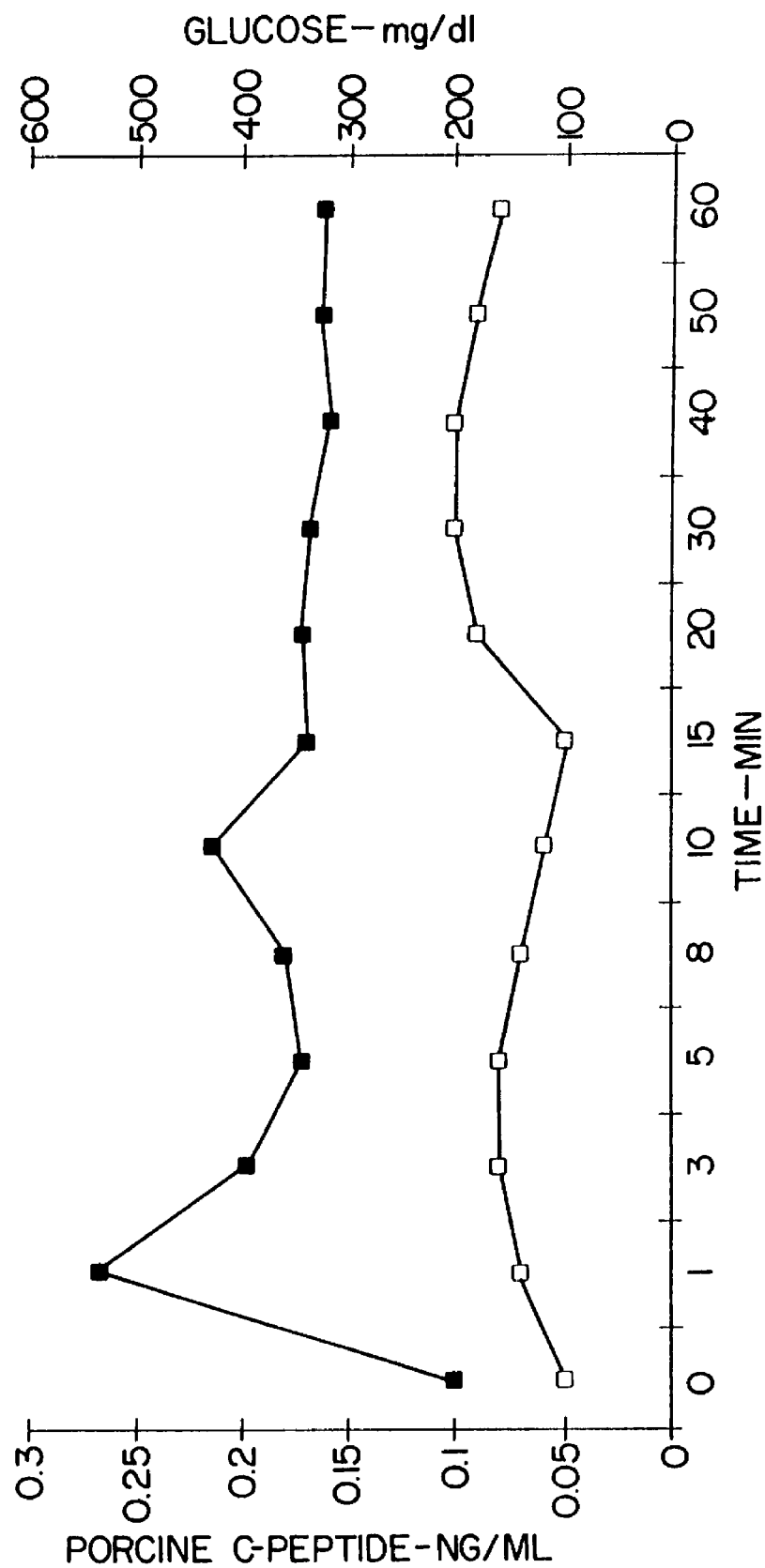
FIG. 20 are intravenous glucose tolerance test (IVGTT) data for the dog of FIG. 17.

In vitro experiments were performed to determine the effect of the described matrix on RNA content, a measure of cellular genetic coding for protein production, and insulin secretory ability. FIG. 18 shows that 5,500 islets isolated 7 days earlier showed maximal insulin secretion, with a nadir of measured total RNA. Likewise, on Day 21, total RNA reached maximal concentrations while there was only minimal insulin secretory function. During the measured times, islet viability remained constant. These data suggest an inverse cycling of RNA production with insulin secretory ability over time, such that as mRNA increases, insulin secretion increases and vice-versa. These in vitro data are supported by IVGTT C-peptide measurement in the experimental annals as described forthwith. After such quiescent periods, C-peptide production resumed at levels substantially the same as or exceeding the levels during prior testing. During one such quiescent period, Day 15, a conventional intravenous glucose tolerance test (IVGTT) was conducted on Dog ASY. The results shown in FIG. 20 demonstrate that the device was capable of producing large amounts of porcine insulin in response to glucose challenge.

Figure 24:
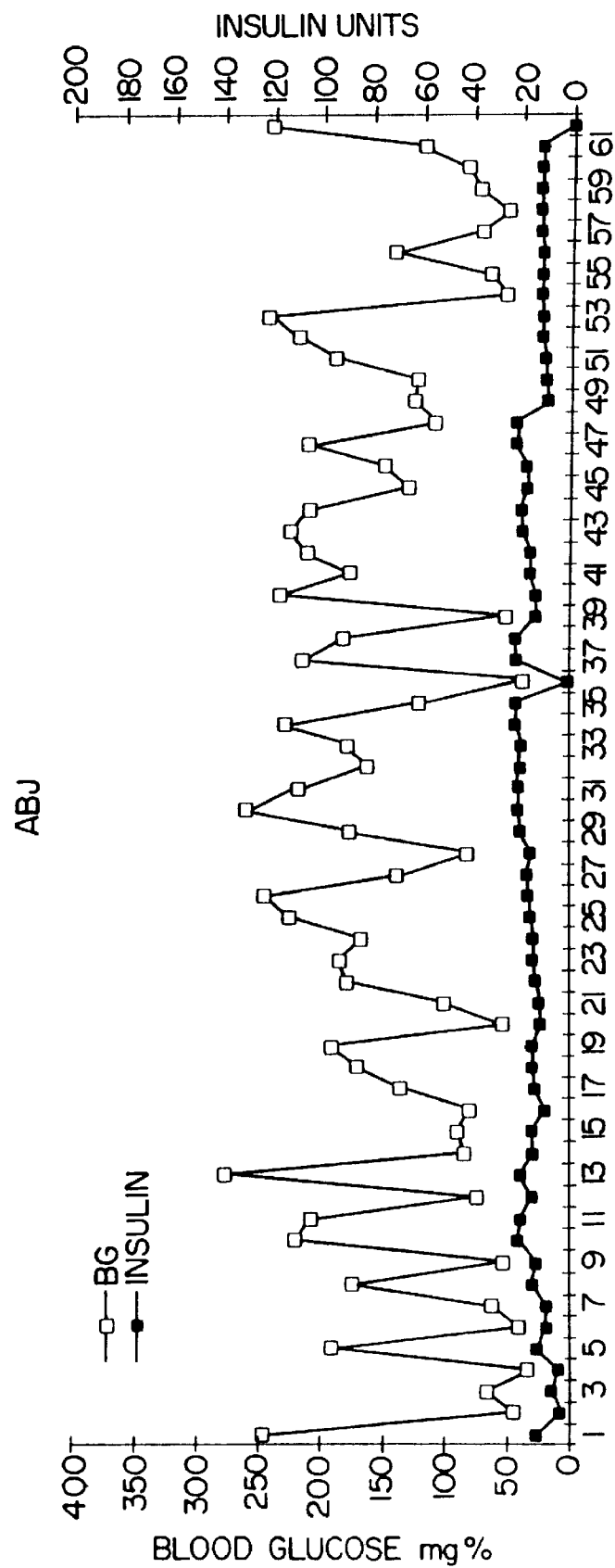
FIG. 24 are IVGTT data for the dog of FIG. 21.
Figure 25:
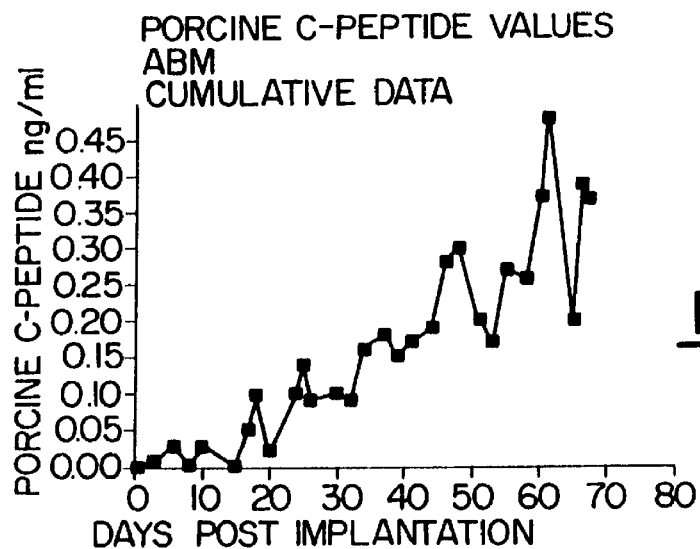
FIGS. 25–30 are maximal serum C-peptide values from a series of test dogs.
Figure 26:
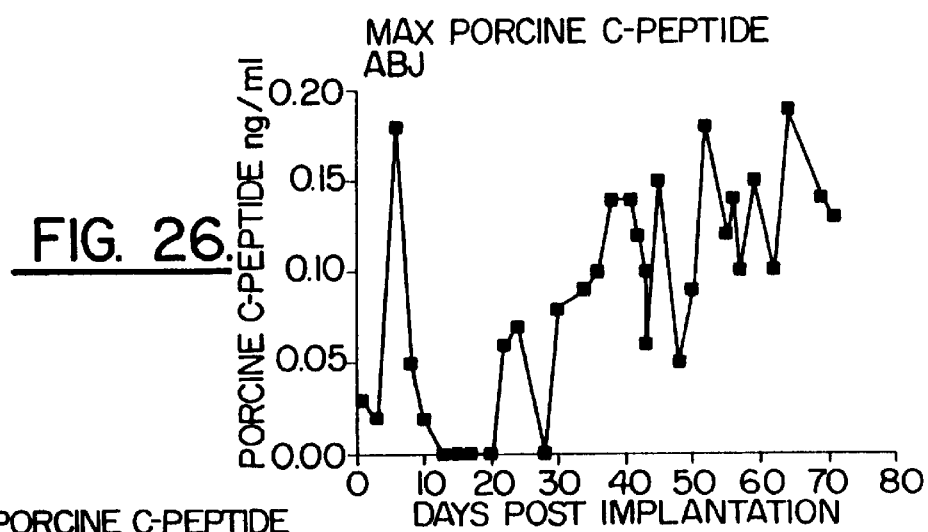
Figure 27:
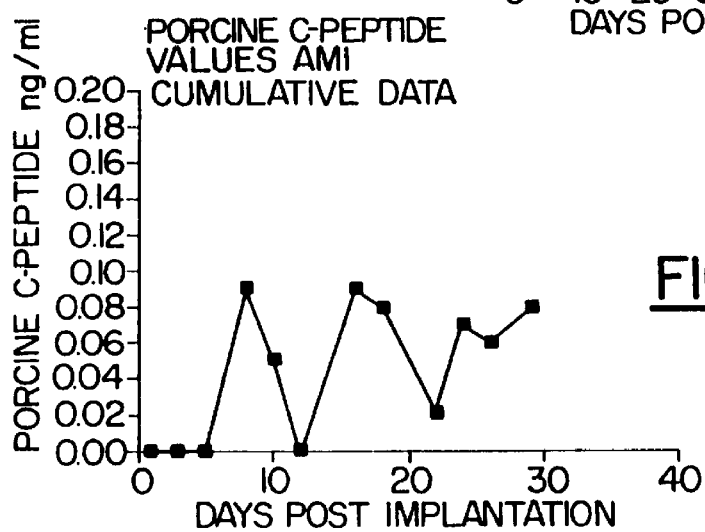
Figure 28:
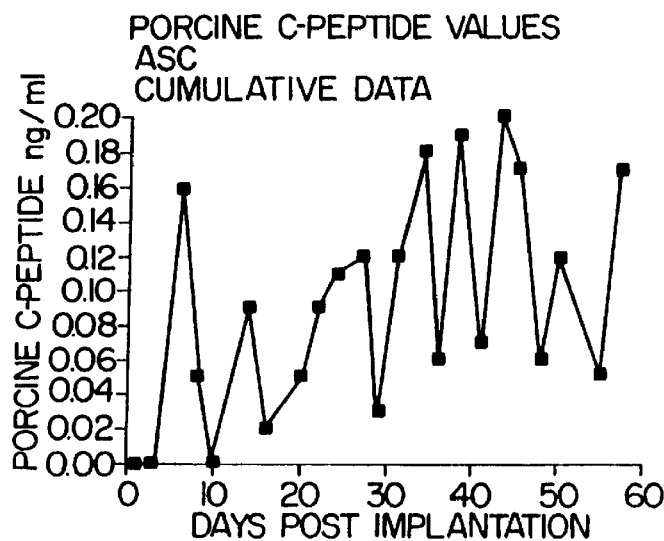
Figure 29:
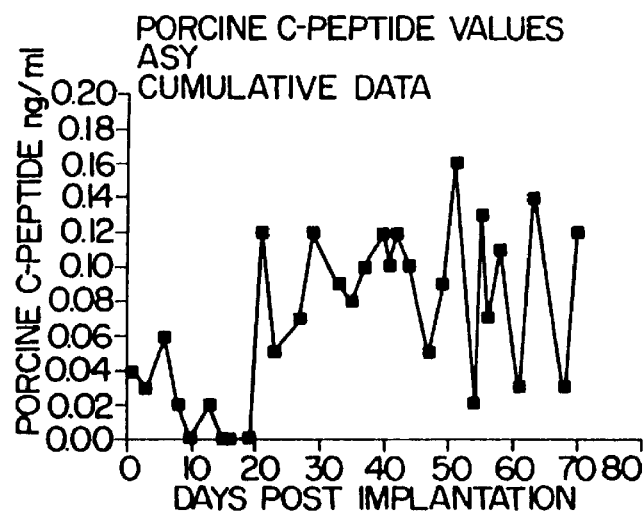
Figure 30:
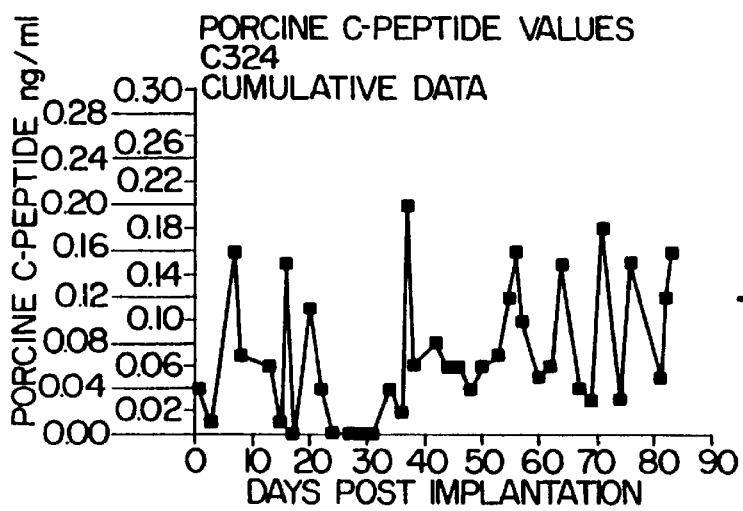

A second dog, Dog ABJ, a 10 kg. purpose bred female Beagle, had the equivalent of four strips containing about 200,000 islets equivalents inserted through an incision intramuscularly along the left dorsal thorax behind the shoulder. Thereafter, the incision was infiltrated with about 20 ml. of non-cellular matrix and the incision closed. Seven days later Dog ABJ received a complete pancreatectomy. Blood glucoses were determined daily. The blood glucose readings are shown in FIG. 24. As with Dog ABY, in order to keep the blood glucose level below about 150 mg/dl substantially throughout the day, Dog ABJ received Ultra-Lente insulin and regular insulin in the noted total amounts.

Figure 23:
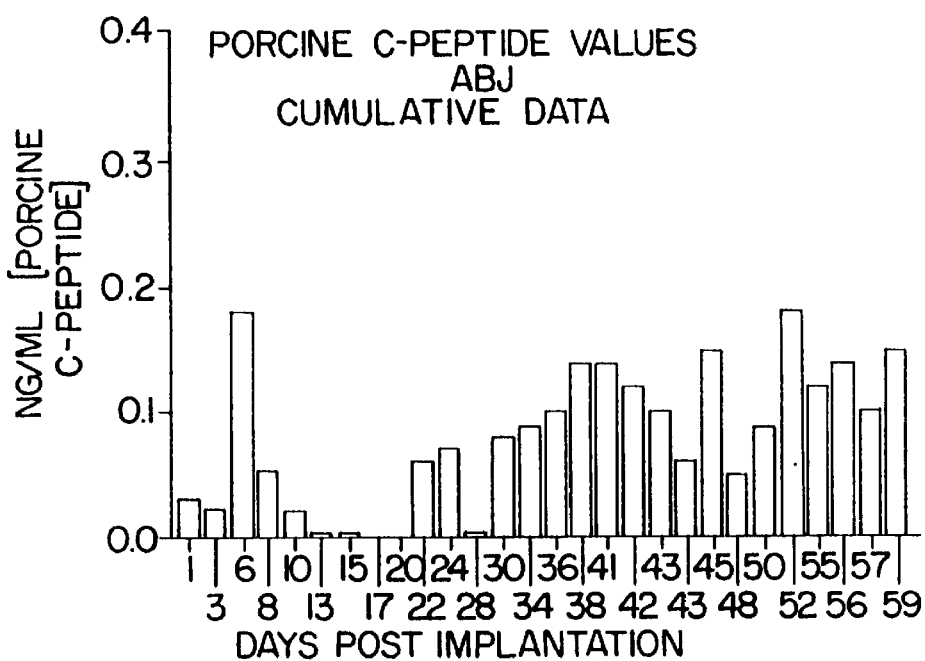
FIG. 23 is a porcine C-peptide versus days post transplant for the dog of FIG. 21.
Figure 21A:
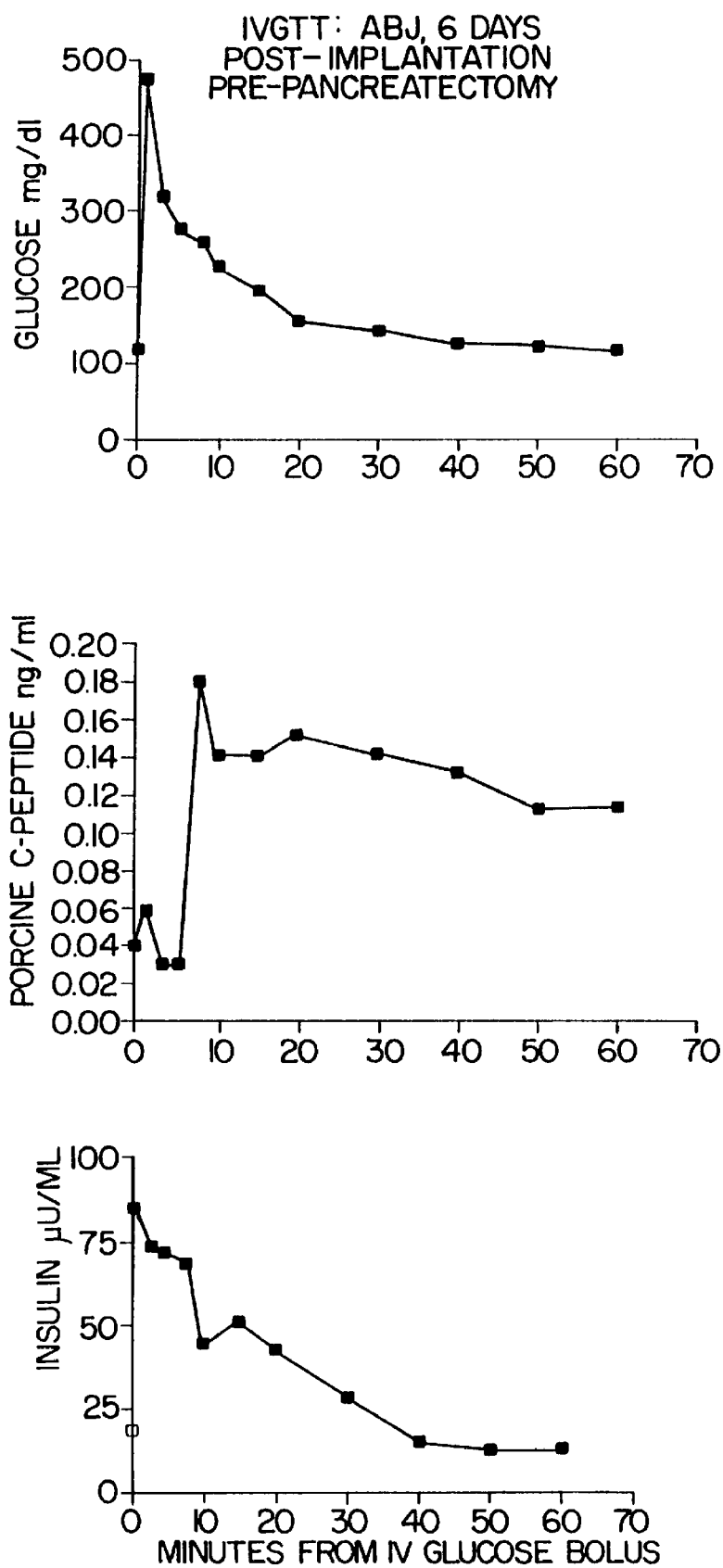
FIGS. 21A and 21B are IVGTT data on a dog at 40 and 57 days post transplant.
Figure 21B:
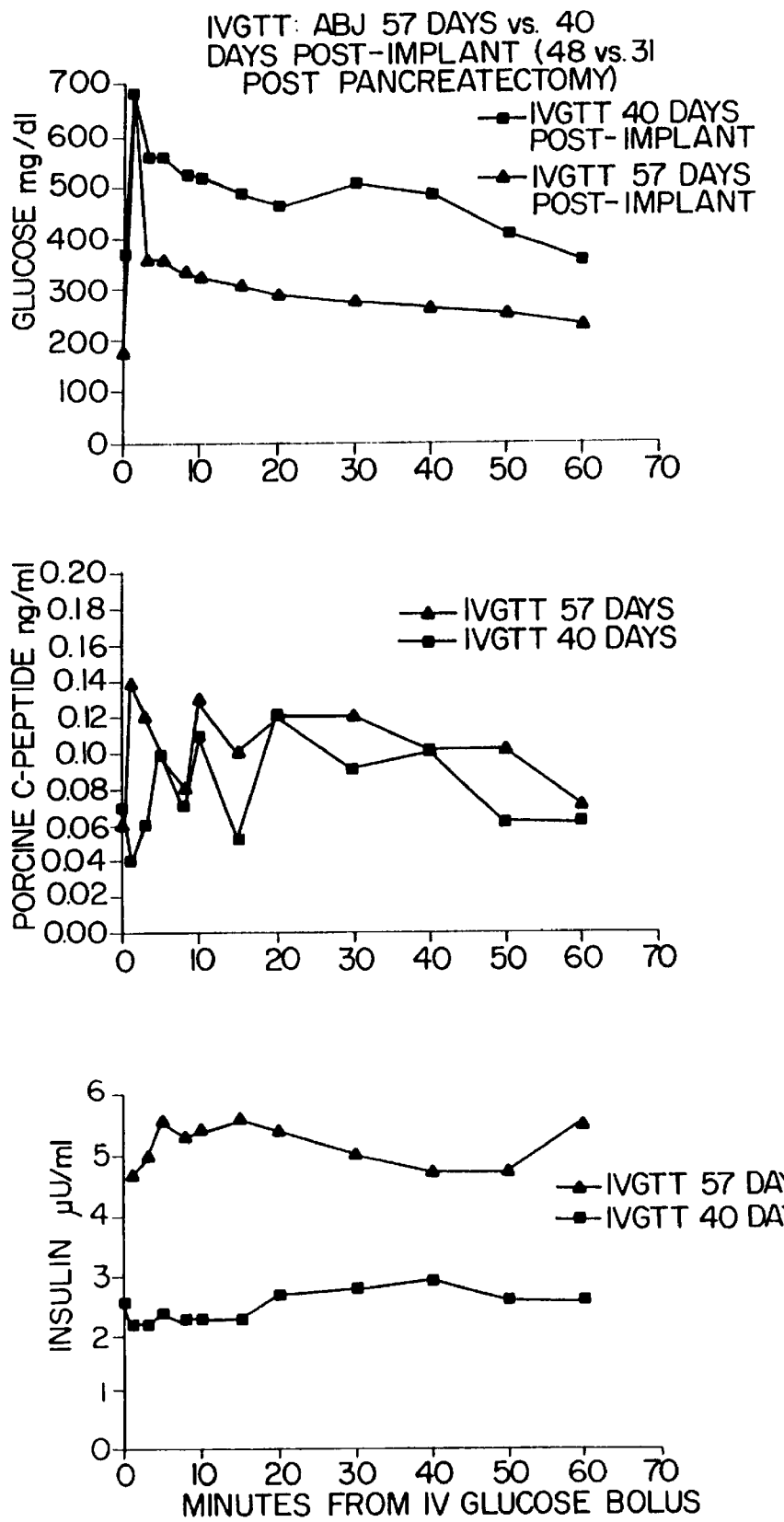

C-peptide levels were also periodically determined and the results are shown in FIG. 23 and FIGS. 21A and 21B. Therein, the devices were implanted on Day 1 and the pancreas removed on Day 8. During the period before the pancreas was removed, porcine C-peptide was detected in the blood samples, with levels rising from 0.04 to 0.18 ng/ml in response to the standard 0.5 g/kg IV glucose bolus. Throughout the trial, detectable levels were determined except for quiescent periods. After such quiescent periods, C-peptide production resumed at levels substantially the same as or exceeding the levels during prior testing. FIG. 21B shows the IVGTT glucose, C-peptide, and total insulin values for Dog ABJ on 40 and 57 days post implantation (31 and 48 days after pancreas removal). On Day 40, the maximal glucose level was 692 and on Day 57 690 mg/dl one minute after the glucose bolus. However, by Day 57, the C-peptide had reached maximal first phase release level at one minute, with no significant diminution (0.14 mg/ml) from initial values.

Figure 22A:
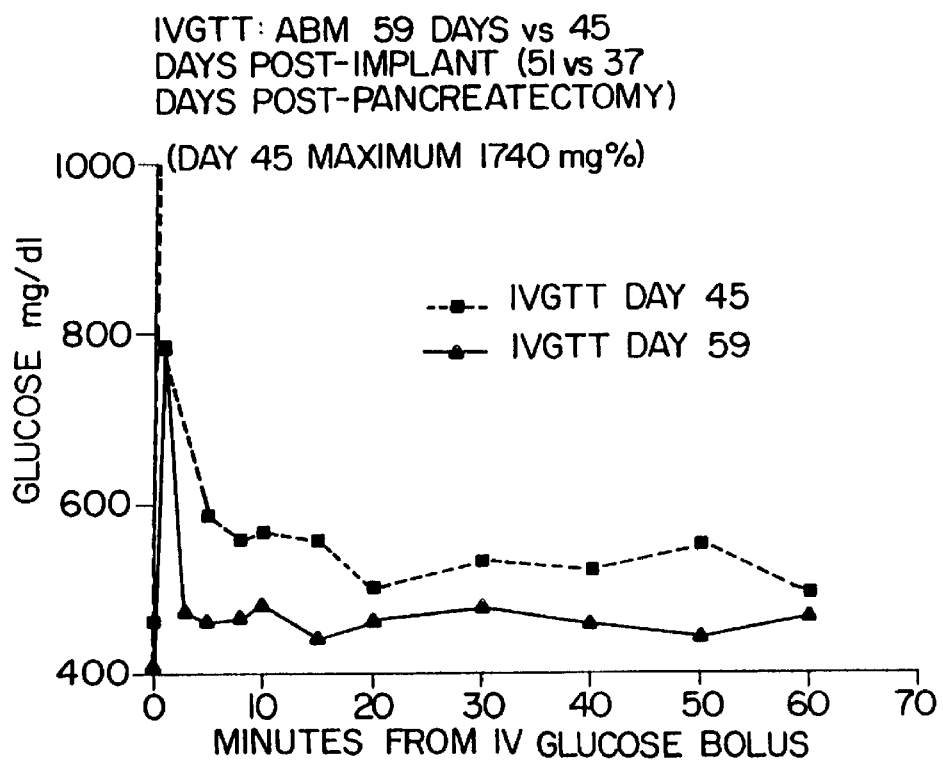
FIGS. 22A and 22B are IVGTT data on another dog at 45 and 59 days post implant.
Figure 22B:
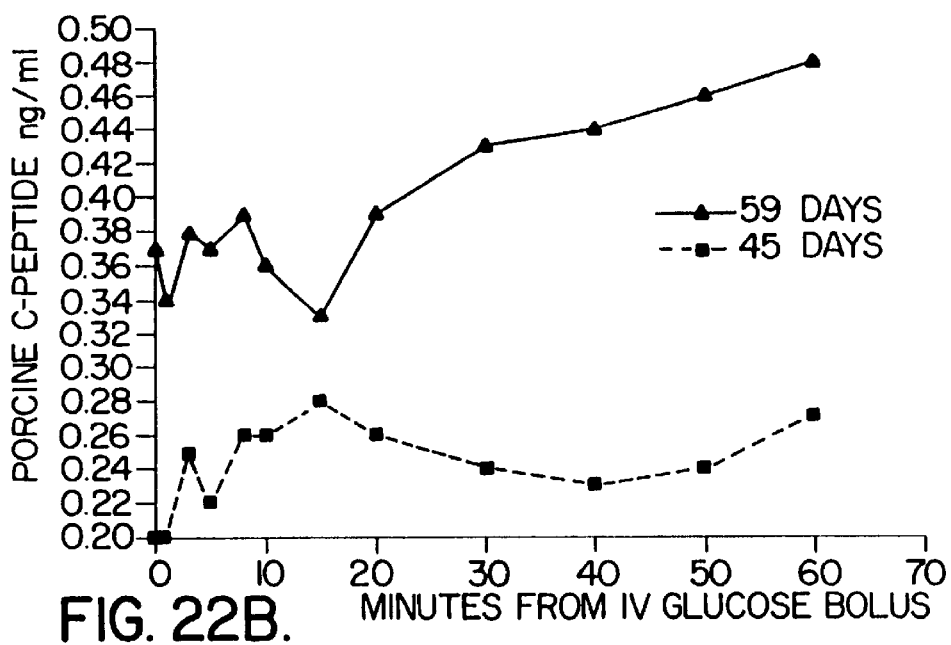

A third beagle subject, ABM, 21 days after implantation and 2 weeks post pancreas removal, had a maximal C-peptides concentration of 0.14 mg/ml. The prepancreatectomy IVGTT data are shown in FIG. 22A. By 45 days, a repeat IVGTT demonstrated a maximal porcine C-peptide concentration of 0.28 mg/ml, and at 59 days, of 0.48 mg/ml (FIG. 22B). As well, ABM's maximal blood glucose fell from 1740 mg/dl to 790 mg/dl in response to the IVGTT glucose bolus.

As mentioned above, it is apparent that the islets thrive and replicate in the matrix formulation. In order to determine the nature of this improvement, an electron microscopy evaluation of the matrix and a mRNA determination were conducted. Referring again to FIGS. 6–11, it is apparent that clusters of islets are attached to and along the collagen strands at Day 74 whereas initial observations revealed minimal such attachment. Improvement is observed in C-peptide production quantities over time both in vivo an in vitro in the previously mentioned matrix. This is associated with islet binding to the collagen infrastructure as occurs in life before such cells can be stimulated to make insulin. The depression in the outer surface of the islet is one of two sites thought to be involved in the binding of the islets to the collagen strands.

To further determine if islet tissue was replicating, a standard tritiated thymidine incorporation experiment was performed on isolated porcine islets cultured in media 199 compared to islets cultured in the aforementioned matrix containing sulfated dextran (5% w/v) Media 199, 5% newborn calf serum, calf skin and porcine skin collagen, dl-cysteine, l-glutamic acid, dl-arginine, and l-arginine analogues (50–100 micro molar) including aminoguanidine, N-monomethyl L-arginine, N nitro-L-arginine which serve as nitric oxide inhibitors. Precursors (tritiated thymidine, 1 microCurie/ml) were proliferated into DNA label over a three day incubation period and subsequently extracted from the tissue. The procedure is based on the method of Levya and Kelley (Analytical Biochemistry 62: 173–9, 1974). Cells were lysed by repeated freeze/thaw treatments in Tris buffer, and the total nucleic acids precipitated and hydrolyzed in perchloric acid. An aliquot of the preparation was used to determine thymidine incorporation as the radioactivity detected by scintillation counting. Another portion was used for quantification of total DNA present using diphenylamine and acetaldehyde to generate color detectable 600 nm.

These studies demonstrated enhanced thymidine incorporation in islets carried for 3 days in matrix compared to traditional surface culture at 4° or 37° C. In addition, comparisons of islets maintained for up to 30 days in these two conditions showed a dramatic difference in proliferative activity with matrix labeled embedded islets incorporating nearly 30-fold the amount seen in medium controls. Duplicate cultures, when analyzed showed very close agreement in label incorporation amounts, for both matrix and medium cultures. Tritiated thymidine incorporation over time was examined and results from two experiments showed a decline in this activity in the early culture period, suggesting a cyclical nature to this process in the period before 30 days, as was seen previously for gene expression and insulin secretion in the islet cultures. DNA quantification results confirmed more than 300 micrograms of DNA from 28,000 islets embedded in the above matrix, and that this content remained stable over 30 days. These data further verify the ability of the matrix to enhance islet viability as well as islet function as measured by insulin secretion.

The addition of the above mentioned nitric oxide inhibitors and scavengers, i.e. L-arginine analogues and sulfated compounds such as dextran, heparin, cysteine, cystine and the like, improve islet survival and secretory function. Some the aforementioned substrates serve dual purposes as mentioned earlier by providing increased structural integrity, but also serve to inhibit nitric oxide formation that results from relative states of islet hypoxia. Thus, islets embedded in the aforementioned matrix because of the nitric oxide inhibition do not exhibit central necrosis even after months of storage in relatively low oxygen states. Nitric oxide serves a protective role in ischemia hyperperfusion injury by binding transition or heavy metals, such as iron or zinc that serve as tactilites for the conversion of super oxide ($O_2$—) to the highly toxic and reactive hydroxyl radical (OH—). Nitric oxide can bind to metal binding sites, thus inhibiting the formation of the more toxic hydroxyl radical, and thus acts as an antioxidant like metal chelators or super oxide dismutase. Addition of EDTA to the matrix serves to inhibit the hydroxyl radical in lieu of the bound nitric oxide which can no longer serve this function.

If cold storage is not required, the aforementioned matrix can be formulated without the addition of boiled collagen, and islets can be maintained for weeks in a more conventional liquid environment at 37° C. The addition of a wide range of sulfated compounds, and L-arginine analogues, enhances the viability of such maintained islets for weeks in sterile culture conditions.

Figure 31:
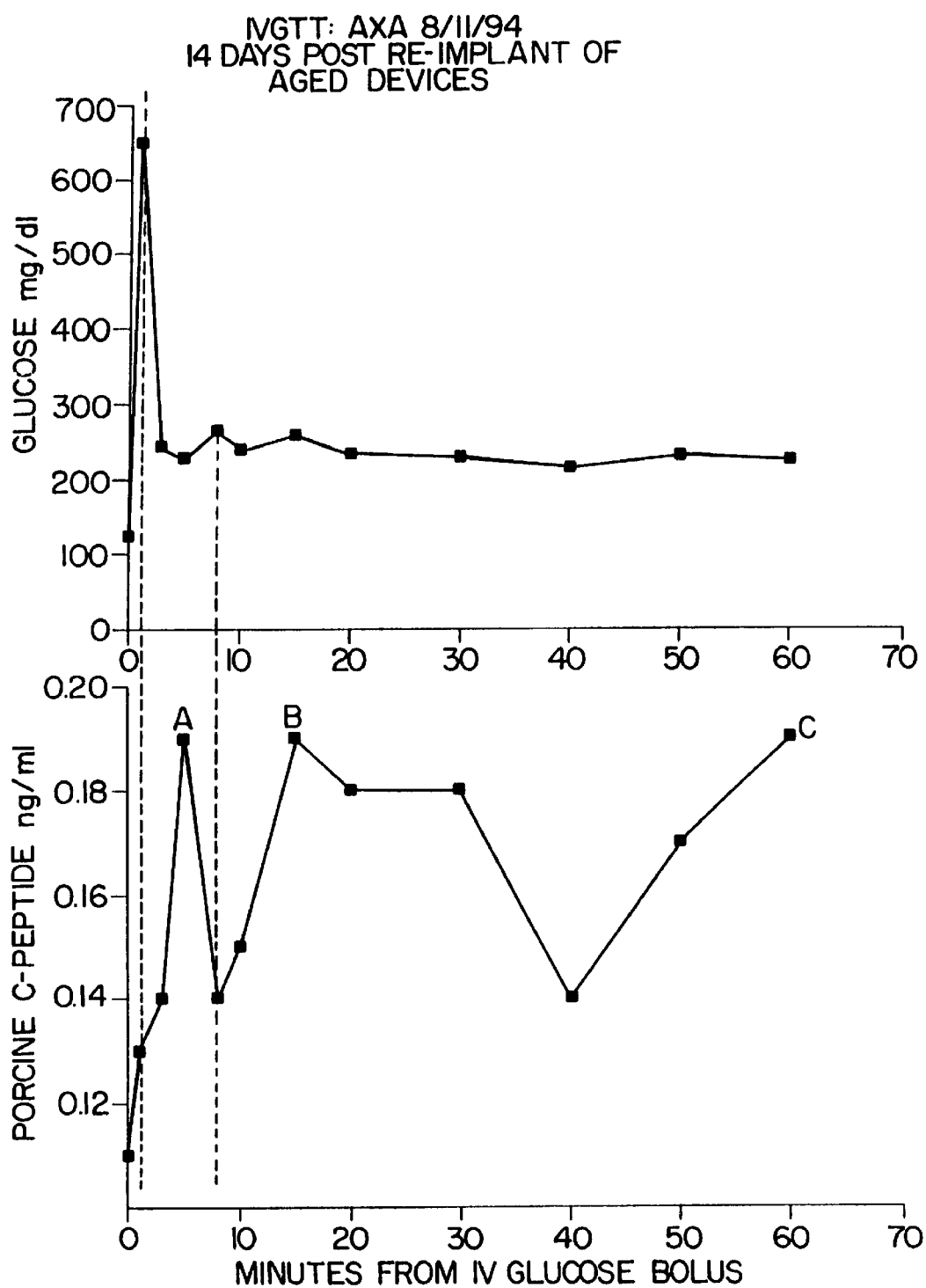
FIG. 31 is an intravenous glucose tolerance test with 21 day old islets re-implanted in Dog AXA after 14 days of implantation, and 50 days after pancreatectomy.
Figure 32:
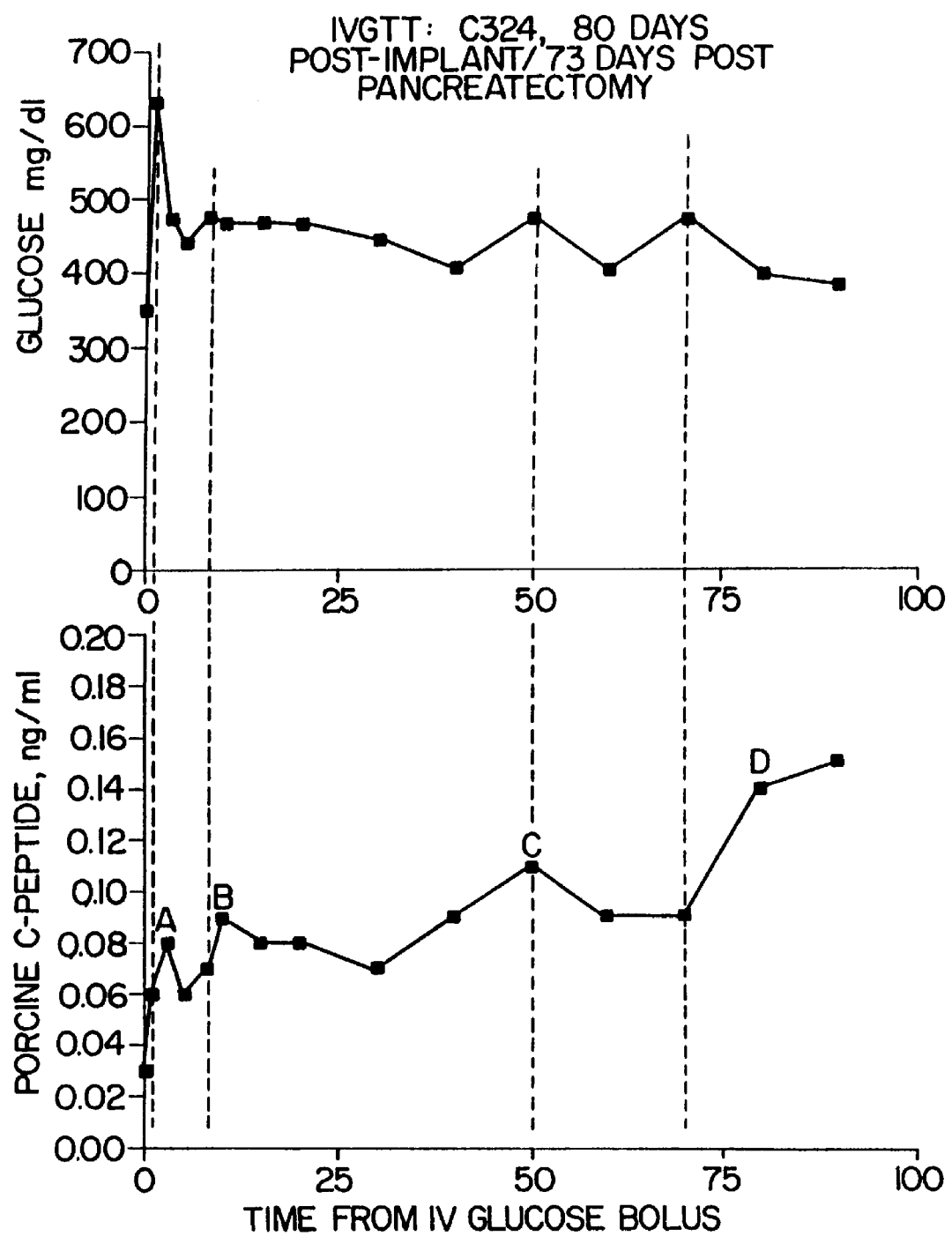
FIG. 32 is an intravenous glucose tolerance test (IVGTT) from Dog C324 80 days after implantation.

In all subject dogs, C-peptide tended to wax and wane over time as per the above cycle, but trended upward (FIGS. 25–30) over time. As found in vitro, most dogs showed a spike of C-peptide on Day 6, then a nadir on Day 21, indicative of the previously described cycling. FIG. 31 shows a brisk C-peptide response in AXA, when the islets were allowed to be kept in culture condition 21 days prior to implantation. Of critical in vivo importance is the ability to the implanted devices to quickly respond with insulin (C-peptide) in response to a glucose challenge, as tested for during the intravenous glucose tolerance test. In FIG. 31, the aged devices (120,000 islet equivalents) demonstrated not only good maximal C-peptide response, but normalization of blood glucose in a dog that had been pancreatectomized 50 days earlier. (The subject's earlier devices were removed to test the viability of aged devices.) The Figure clearly demonstrates the biphasic C-peptide release (A and B) in response to spikes in glucose concentration. This is again shown in subject C324 (FIG. 32), where the implants were 80 days old, with C-peptide peaks resulting from glucose peak stimulus over 90 minutes. These data demonstrate normal insulin pulsatility in vivo which would be of therapeutic benefit to patients with Type II diabetes.

While the aforementioned encapsulation for purposes of describing the preferred embodiments has been; described with reference to the xenographic transplantation of porcine islets, those skilled in the art of cellular transplantation will appreciate that the present invention may be effectively utilized in other applications for hormone producing or tissue producing implantation into deficient individuals with endocrine conditions such as thyroid deficiency, growth hormone deficiency, congenital adrenal hyperplalsia, Parkinson's Disease and the like, and likewise for therapeutic conditions benefitting from implantable delivery systems for biologically active and gene therapy products for the treatment of central nervous system diseases and other chronic disorders. More specifically devices and matrices as described will find application in the various transplantation therapies, including without limitation cells secreting human nerve growth factors for preventing the loss of degenerating chlolingergic neurons, satellite cells for myocardial regeneration, striatal brain tissue for Huntington's disease, liver cells, bone marrow cells, dopamine-rich brain tissue and cells for Parkinson's disease, cholinergic-rich nervous system for Alzheimer's disease, adrenal chromaffin cells for delivering analgesics to the central nervous system, cultured epithelium for skin grafts, and cells releasing ciliary neurotropic factor for amyotrophic lateral sclerosis. Thus, various modifications of the above described embodiments will be apparent to those skilled in the art. Accordingly, the scope of the invention is defined only by the accompanying claims.

What is claimed:

1. An improved storage matrix for prolonging the functional survival of cellular tissue, comprising: denatured collagen and intact collagen for providing binding sites for said tissue in an amount of about 0.01 to 30 mM; a liquid in a n amount of about 15 to 96.5 percent by weight; a polymeric buffer substrate for reducing cellular damage to said islets at said storage temperature in an amount of about 0.01 to 1000 micromolar, wherein said substrate forms a membrane coating having a porosity to permit passage of nutrients and biological agents and prevent passage of immunogenic agents.

2. The matrix as recited in claim 1 wherein said polymeric buffer substrate is a long chain carbohydrate based polymer sugar.

3. The matrix as recited in claim 2 wherein said polymeric buffer substrate is dextran.

4. The matrix as recited in claim 1 wherein said polymeric substrate is amylopectin.

5. The matrix as recited in claim 1 wherein said polymeric substrate is a polymeric proteoglycan.

6. The matrix as recited in claim 1 wherein said nitric oxide inhibitor is a sulfanated moiety protecting protecting the tissue from hypoxic, chemical, thermal, or mechanical trauma.

7. The matrix as recited in claim 6 wherein said nitric oxide savenger is selected from the group comprising dextran, heparin, cysteine, and cystine.

8. The matrix as recited in claim 7 wherein said nitric oxide inhibitor is an L-arginine analog.

9. The matrix as recited in claim 8 wherein said l-arginine analog is selected from the group comprising aminoguanidine, N-monoethyl L-arginine, N-nitro-L-arginine, or D-arginine functioning to replace L-arginine as a substrate for nitric oxide formation.

10. A hydrogel matrix suitable for long term storage of cellular tissue comprising from about 15 to 96.5 percent by weight of an aqueous nutrient solution containing 0.001 to 100 mM collagen 0.01 to 1000 micromolar cryoprotectant 0.001 to 100 mM divalent chelator 0.01 micromolar to 300 mM nitric oxide inhibitor.

11. The matrix of claim 10 wherein the collagen is a denatured collagen.

12. The matrix of claim 10 wherein the coliagen is a combination of denatured collagen and native collagen.

13. The matrix of claim 10 wherein the cryoprotectant i s a long chain carbohydrate based sugar.

14. The matrix of claim 10 wherein the cryoprotectant is selected from the group consisting of dextran, sulfated dextran, anylopectin and proteoglycan.

15. The matrix of claim 10 wherein the nitric oxide inhibitor is an amino acid.

16. The matrix of claim 10 wherein the nitric oxide inhibitor is selected from the group consisting of dextran, heparin, cysteine and cystine.

17. The matrix of claim 10 wherein the nitric oxide inhibitor is an L-arginine analog.

18. The matrix of claim 17 wherein said L-arginine analog is selected from the group consisting of aminoguanidine, N-monoethyl L-arginine and N-nitro-L-arginine.

19. The matrix of claim 10 wherein the divalent chelator is selected from the group consisting of citrate, EDTA and EGTA.

20. The matrix of claim 10 wherein the nutrient solution includes a water soluble protein.

21. The matrix of claim 10 additionally comprising an antibiotic.

22. The hydrogel matrix of claim 10 characterized in that said matrix is a solid at 4° C. and a liquid at 37° C.

23. A storage matrix for prolonging the functional survival of cellular tissue comprising collagen in an amount sufficient to provide a structural rigidity, water, and a polymeric buffer to provide a membrane coating having a porosity to permit passage of nutrients and biological agents and prevent passage of immunogenic agents.

24. The matrix of claim 23, wherein said collagen is a denatured collagen.

25. The matrix of claim 23, wherein said collagen is a combination of denatured collagen and native collagen.

26. The matrix of claim 23, further comprising a divalent chelator.

27. The matrix of claim 25, further comprising a nitric oxide inhibitor.

28. The matrix of claim 26, further comprising a nitric oxide inhibitor.

29. The matrix of claim 25, further comprising a cryoprotectant.

30. The matrix of claim 28, further comprising a cryoprotectant.

31. The matrix of claim 30, wherein said cryoprotectant is a long chain carbohydrate-based sugar.

32. The matrix of claim 31, wherein said cryoprotectant is selected from the group consisting of dextran, sulfated dextran, amylopectin and proteoglycan.

33. The matrix of claim 28, wherein said nitric oxide inhibitor is an amino acid.

34. The matrix of claim 28, wherein said nitric oxide inhibitor is selected from the group consisting of dextran, heparin, cysteine and cystine.

35. The matrix of claim 33, wherein said nitric oxide inhibitor is an L-arginine analog.

36. The matrix of claim 35, wherein said L-arginine analog is selected from the group consisting of aminoguanidine, N-monoethyl L-arginine, and N-nitro-L-arginine.

37. The matrix of claim 26, wherein said divalent chelator is selected from the group consisting of citrate, EDTA, and EGTA.

38. The matrix of claim 23, further comprising an antibiotic.

39. A method for prolonging the functional survival of cellular tissue, said method comprising placing said tissue in a storage matrix comprising a combination of denatured collagen and native collagen in an amount sufficient to provide a structural rigidity, and a polymeric buffer to provide a membrane coating having a porosity to permit passage of nutrients and biological agents and prevent the passage of immunogenic agents.

40. The method of claim 39, wherein said matrix further comprises a divalent chelator.

41. The method of claim 40, wherein said matrix further comprises a nitric oxide inhibitor.

42. The method of claim 41, wherein said matrix further comprises a cryoprotectant.

43. The method of claim 40, wherein said matrix further comprises a cryoprotectant.

44. The method of claim 43, wherein said cryoprotectant is a long chain carbohydrate-based sugar.

45. The method of claim 43, wherein said cryoprotectant is selected from the group consisting of dextran, sulfated dextran, amylopectin and proteoglycan.

46. The method of claim 41, wherein said nitric oxide inhibitor is an amino acid.

47. The method of claim 41, wherein said nitric oxide inhibitor is selected from the group consisting of dextran, heparin, cysteine and cystine.

48. The method of claim 46, wherein said nitric oxide inhibitor is an L-arginine analog.

49. The method of claim 48, wherein said L-arginine analog is selected from the group consisting of aminoguanidine, N-monoethyl L-arginine, and N-nitro-L-arginine.

50. The method of claim 40, wherein said divalent chelator is selected from the group consisting of citrate, EDTA, and EGTA.

51. The method of claim 39, wherein said matrix further comprises an antibiotic.

* * * * *